(12) United States Patent
Karri et al.

(10) Patent No.: US 11,718,584 B2
(45) Date of Patent: Aug. 8, 2023

(54) PROCESS FOR THE SYNTHESIS ANTHRANILIC DIAMIDE COMPOUNDS AND INTERMEDIATES THEREOF

(71) Applicant: PI INDUSTRIES LTD., Udaipur-Rajasthan (IN)

(72) Inventors: Phaneendrasai Karri, Guntur-Andhra Pradesh (IN); Jagadish Pabba, Udaipur-Rajasthan (IN); Bharat Uttamrao Shinde, Dist-A.Nagar-Maharashtra (IN); Amol Dnyaneshwar Kalwaghe, Dist-A.Nagar-Maharashtra (IN); Kamble Maruti Madhavrao, Dist: Latur-Maharashtra (IN); Alexander G. M. Klausener, Pulheim (DE); Deepak Shankar Panmand, Ahmednagar-Maharashtra (IN)

(73) Assignee: PI INDUSTRIES LTD., Udaipur-Rajasthan (IN)

( * ) Notice: Subject to any disclaimer, the term of this patent is extended or adjusted under 35 U.S.C. 154(b) by 194 days.

(21) Appl. No.: 17/310,712

(22) PCT Filed: Feb. 20, 2020

(86) PCT No.: PCT/IB2020/051410
§ 371 (c)(1),
(2) Date: Aug. 19, 2021

(87) PCT Pub. No.: WO2020/170178
PCT Pub. Date: Aug. 27, 2020

(65) Prior Publication Data
US 2022/0185782 A1  Jun. 16, 2022

(30) Foreign Application Priority Data
Feb. 22, 2019 (IN) .............................. 201911007091

(51) Int. Cl.
*C07D 231/10* (2006.01)
*C07C 227/18* (2006.01)

(52) U.S. Cl.
CPC .......... *C07D 231/10* (2013.01); *C07C 227/18* (2013.01)

(58) Field of Classification Search
CPC .................................................. C07D 231/10
(Continued)

(56) References Cited

U.S. PATENT DOCUMENTS 7,528,260 B2 * 5/2009 Shapiro ................ C07D 231/16
562/622

* cited by examiner

Primary Examiner — Taofiq A Solola
(74) Attorney, Agent, or Firm — Lippes Mathias LLP

(57) ABSTRACT

The present invention disclosed a process for the synthesis of anthranilic diamide compound of formula (I),

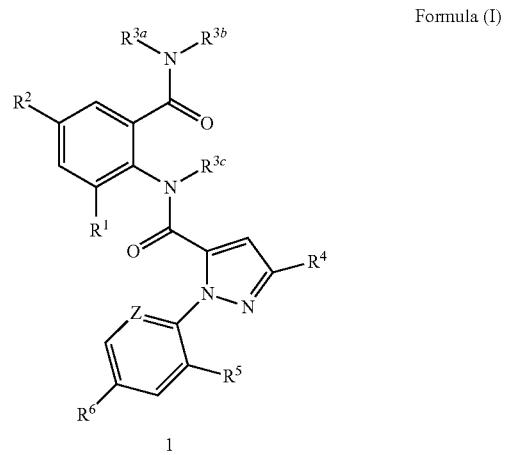

Formula (I)

wherein, $R^1$, $R^2$, $R^{3a}$, $R^{3b}$, $R^{3c}$, $R^4$, $R^5$, $R^6$ and Z are as defined in the detailed description. The process comprising the step of obtaining a mono- or dicyano substituted aniline compound of formula (IV) which is then converted to an anthranilic acid compound of formula (V) or an anthranilic amide compound of formula (Va). Further, the compound of formula (VI) can be optionally synthesized from compound of formula (IV or V or Va)

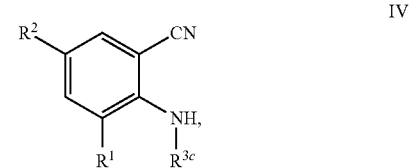

IV

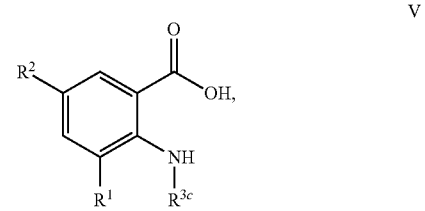

V

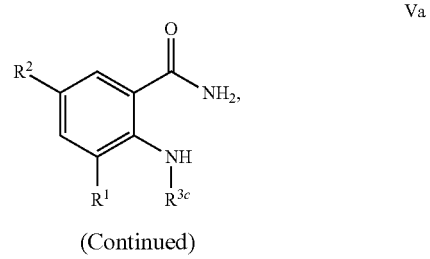

Va (Continued)

-continued
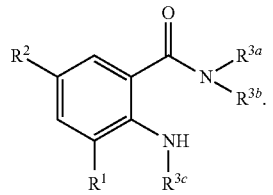
VI
19 Claims, No Drawings
(58) Field of Classification Search
USPC .................................................. 548/374.1
See application file for complete search history.

PROCESS FOR THE SYNTHESIS ANTHRANILIC DIAMIDE COMPOUNDS AND INTERMEDIATES THEREOF

This application is a National Stage Entry of International Application No. PCT/IB2020/051410, filed Feb. 20, 2020, and entitled "A PROCESS FOR THE SYNTHESIS ANTHRANILIC DIAMIDE COMPOUNDS AND INTERMEDIATES THEREOF;" which claims priority to Indian Application No. 201911007091, filed Feb. 22, 2019, and entitled "A PROCESS FOR THE SYNTHESIS ANTHRANILIC DIAMIDE COMPOUNDS AND INTERMEDIATES THEREOF," the contents of which are incorporated by reference herein.

FIELD OF THE INVENTION

The present invention relates to a process for the synthesis of anthranilic diamide compounds. More particularly, the present invention relates to a process for the synthesis of anthranilic diamide compound of formula (I) from substituted aniline compound of formula (II). The present invention further relates to a process for the synthesis of intermediates which are useful in the synthesis of compound of formula (I), from substituted aniline compound of formula (II).

BACKGROUND OF THE INVENTION

Anthranilic diamides are a commercially important class of synthetic insecticides that bind to the ryanodine receptor with selective potency against insect versus mammalian forms of the receptor. The first commercialized anthranilic diamide of this class, chlorantraniliprole, has exceptional activity against lepidopteran pests. The second anthranilic diamide product of the same class, cyantraniliprole, has excellent cross-spectrum activity against a range of insect orders, including both lepidopteran and hemipteran pests. The PCT publications WO2003015518, WO2003015519, WO2004067528, WO2005077934, and WO20100069502 disclose the use of anthranilic diamides for controlling invertebrate pests such as arthropods.

These anthranilic diamide compounds can be prepared from 3,5-substituted 2-amino-N-alkylbenzamide compounds as intermediates. The PCT publication WO2013007603 discloses a process for preparation of 2-amino-5-cyano-3-methyl (N-methyl) benzamide compounds from 2-amino-5-cyano-3-methylbenzoic acid esters. Further, the synthesis of certain 3,5-substituted 2-amino-N-alkyl-benzamide compounds and their utility as intermediates for preparing corresponding insecticidal anthranilic diamide compounds has been disclosed in WO2004067528, WO2006068669, WO2006062978 and WO2012103436. Further, the process for the synthesis of cyano derivatives of anthranilic diamide compounds or cyano functions containing intermediates thereof are disclosed in PCT publications WO2008010897, WO2008070158, WO2009085816, WO2009061991, WO2009006061 and WO2008082502.

However, the processes described in the above mentioned literature are laborious, and there is still need to find a simple, efficient, and industrially economical process for the preparation of anthranilic diamide compounds. Accordingly, the present invention provides a simple, environment-friendly, and cost-effective process for the preparation of anthranilic diamide compounds and intermediates thereof.

OBJECTIVE OF THE INVENTION

The main objective of the present invention is to provide a simple, environment-friendly and cost-effective process for the synthesis of anthranilic diamide compound of formula (I).

Another objective of the present invention is to provide a process for the synthesis of anthranilic acid compound of formula (V) and anthranilic amide compound of formula (Va).

Yet another objective of the present invention is to provide a process for the synthesis of N-substituted anthranilic amide compound of formula (VI).

SUMMARY OF THE INVENTION

Accordingly, the present invention provides a process for the synthesis of anthranilic diamide compound of formula (I),

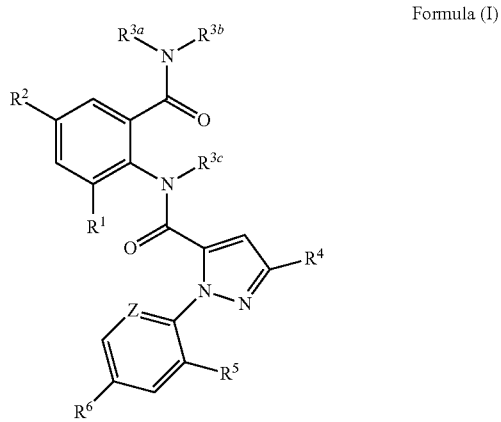

Formula (I)

wherein, $R^1$ is $C_1$-$C_4$ alkyl or halogen;

$R^2$ is hydrogen, halogen or cyano;

$R^{3a}$ and $R^{3b}$ are independently hydrogen, $C_1$-$C_4$ alkyl or $C_3$-$C_6$ cycloalkyl-$C_1$-$C_4$ alkyl;

$R^{3c}$ is hydrogen or $C_1$-$C_4$ alkyl;

$R^4$ is halogen, $CF_3$, $OCF_2H$, $OCH_2CF_3$, or

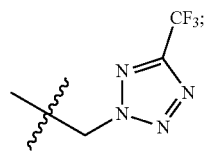

$R^5$ is halogen;

$R^6$ is hydrogen or halogen;

Z is $CR^7$ or N; and $R^7$ is hydrogen or halogen, from substituted aniline compound of formula (II);

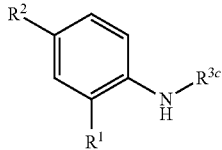

wherein, $R^1$, $R^2$ and $R^{3c}$ have the above mentioned definition.

The process for the synthesis of anthranilic diamide compound of formula (I) comprises a step of obtaining a mono- or dicyano substituted aniline compound of formula (IV) which is then converted to an anthranilic acid compound of formula (V) or an anthranilic amide compound of formula (Va). Finally, the compound of formula (VI) can be optionally synthesized from compound of formula (IV or V or Va).

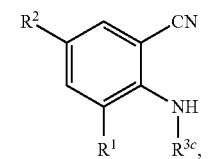

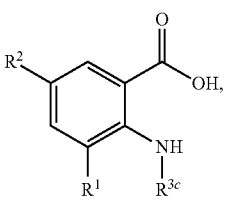

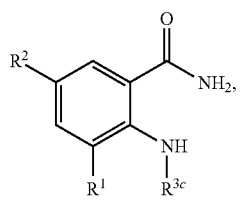

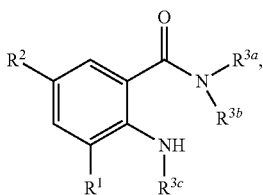

In one embodiment, the present invention provides a process for the synthesis of an anthranilic acid compound of formula (V) or an anthranilic amide compound of formula (Va) from substituted aniline compound of formula (II).

In another embodiment, the present invention provides a process for the synthesis of an N-substituted anthranilic amide compound of formula (VI) from substituted aniline compound of formula (II).

DETAILED DESCRIPTION OF THE INVENTION

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be non-restrictive regarding the number of instances (i.e. occurrences) of the element or component. Therefore "a" or "an" should be read to include one or at least one, and the singular word form of the element or component also includes the plural unless the number is obviously meant to be singular.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and o to 3 heteroatoms. Of note are carbon-based radicals selected from $C_1$-$C_6$ alkyl, $C_1$-$C_6$ haloalkyl and phenyl optionally substituted with 1-3 substituents selected from $C_1$-$C_3$ alkyl, halogen and nitro.

The meaning of various terms used in the description shall now be illustrated.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_{24}$ alkyl, preferably $C_1$ to $C_{15}$ alkyl, more preferably $C_1$ to $C_{10}$ alkyl, most preferably $C_1$ to $C_6$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "cycloalkyl" means alkyl closed to form a ring. Representative examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere.

The term "cycloalkyl" means alkyl closed to form a ring. Representative examples include but are not limited to cyclopropyl, cyclobutyl, cyclopentyl and cyclohexyl.

The term "cycloalkylalkyl" means cycloalkyl substituent on alkyl, for example, cyclopropyl or cyclobutyl or cyclopentyl are substituted on any carbon of $C_1$-$C_6$ alkyl. Representative examples of cycloalkylalkyl include cyclopropyl methyl, cyclopropyl ethyl.

As used herein, the term "combining" refers to the act of "mixing", "intermixing" or "putting together" for the purposes of bringing two or more chemical compounds in close contact so as to promote a chemical reaction. For example certain substrates, reagents or ingredients, reagents as described in the summary of the invention are "combined" with each other in an appropriate vessel, container or apparatus in such a fashion that the substrates, reagents or ingredients can chemically react with one another so that a new product can be formed.

To achieve at least one of the above defined objectives, the present invention provides a process for the synthesis of anthranilic diamide compound of formula (I), Formua (I)

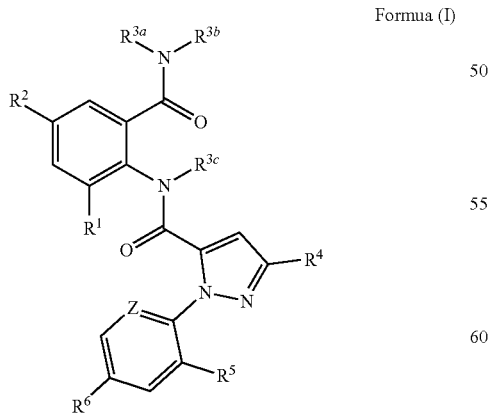

wherein,
$R^1$ is $C_1$-$C_4$ alkyl or halogen;
$R^2$ is hydrogen, halogen or cyano;

$R^{3a}$ and $R^{3b}$ are independently hydrogen, $C_1$-$C_4$ alkyl or $C_3$-$C_6$ cycloalkyl-$C_1$-$C_4$ alkyl;

$R^{3c}$ is hydrogen or $C_1$-$C_4$ alkyl;

$R^4$ is halogen, $CF_3$, $OCF_2H$, $OCH_2CF_3$, or

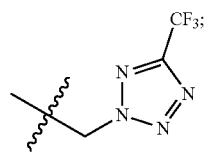 [SMILES: *Cn1nnc(C(F)(F)F)n1]

$R^5$ is halogen;
$R^6$ is hydrogen, halogen;
Z is $CR^7$ or N; and
$R^7$ is hydrogen or halogen, comprising the steps of:

a) reacting a N-substituted anthranilic amide compound of formula (VI) with a pyrazole acid compound of formula (VII) to obtain the compound of formula (I),

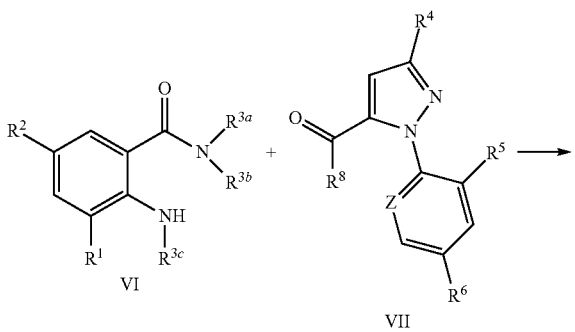

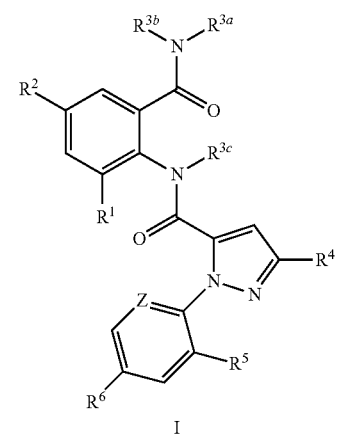

wherein, $R^8$ is OH, Cl, or O—$C_1$-$C_4$ alkyl;

b) converting an anthranilic amide compound of formula (Va) into the N-substituted anthranilic amide compound of formula (VI) by either of the following steps:

i. in the presence of a suitable base or a suitable acid and a suitable alkylating reagent, ii. by using suitable transamidation process, according to the reaction scheme as depicted below:

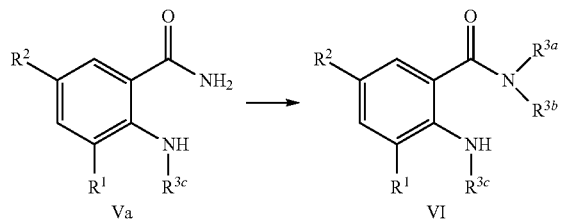

or converting an anthranilic acid compound of formula (V) into the N-substituted anthranilic amide compound of formula (VI) using a suitable amine of formula $HN(R^{3a})(R^{3b})$ and a suitable coupling reagent, according to the reaction scheme as depicted below:

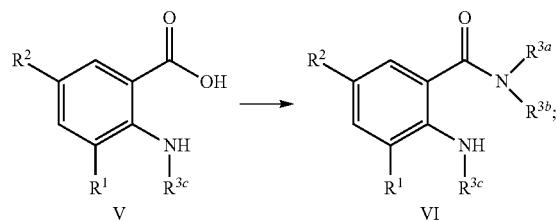

c) converting a mono- or dicyano substituted aniline compound of formula (IV) into the anthranilic acid compound of formula (V) or the anthranilic amide compound of formula (Va) optionally in the presence of a suitable base or a suitable acid, according to the reaction scheme as depicted below:

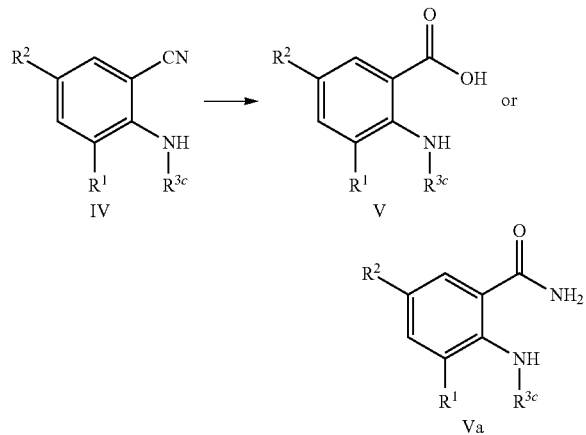

or converting a mono- or dicyano substituted aniline compound of formula (IV) into the N-substituted anthranilic amide compound of formula (VI) by either of the following reaction steps:
  i) in the presence of a suitable base or a suitable acid and a suitable alkylating reagent,
  ii) aminolysis using a suitable amine of formula $HN(R^{3a})(R^{3b})$, according to the reaction scheme as depicted below:

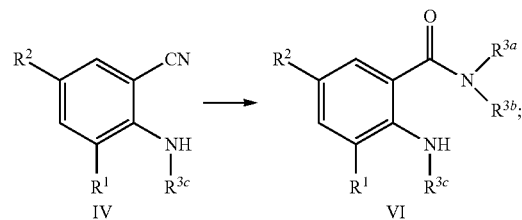

d) optionally, halogenating a mono- or dicyano substituted aniline compound of formula (IV), wherein $R^1$ and/or $R^2$ are hydrogen in the presence of a suitable halogenating agent to obtain a mono- or dicyano substituted aniline compound of formula (IV), wherein $R^1$ and/or $R^2$ are halogen;

e) converting a mono-, di-, or tri-halogenated aniline compound of formula (III) wherein X is halogen, into the mono- or dicyano substituted aniline compound of formula (IV) using a suitable cyanation reagent, according to the reaction scheme as depicted below:

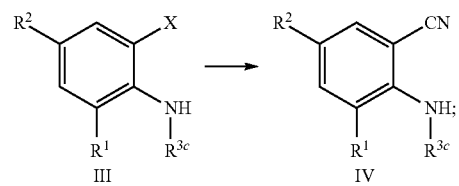

f) converting a substituted aniline compound of formula (II) into the mono-, di-, or tri-halogenated aniline compound of formula (III) wherein X is halogen, using a suitable halogenating agent, according to the reaction scheme as depicted below:

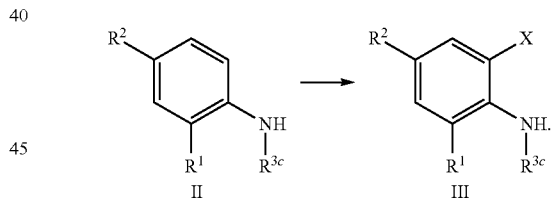

The compound of formula (VII) can be synthesized by using any of the method known in the prior art. For instance the process for synthesis of compound of formula (VII) is disclosed in documents WO2003015518, WO20030155519, WO2011157664 and WO2013030100.

The compound of formula (VI) can be converted into the compound of formula (I) by using any of the suitable method known in the prior art. For instance, the process for converting compound of formula (VI) to the compound of formula (I) is disclosed in the PCT patent applications WO2012103436, WO2008010897 and WO2006062978.

The compound of formula (V) can be converted into a compound of formula (VI) by using any of the suitable method known in the prior art. For instance, the process for converting a compound of formula (V) to a compound of formula (VI) is disclosed in the prior art documents CN106146414A, WO2016131098, *ACS Med. Chem. Lett.*, 2017, 8 (6), pp 678-681 and *Chem. Comm.*, 2018, 54, 12766-12769.

In one embodiment, an anthranilic amide compound of formula (Va) is converted into a N-substituted anthranilic amide compound of formula (VI) by reacting said anthranilic amide compound of formula (Va) in a suitable solvent with a suitable alkylating agent in the presence of a suitable base at a temperature within the range of 20° C. to 100° C. for a period of 1 to 5 h to obtain a N-substituted anthranilic amide compound of formula (VI).

The suitable alkylating agent used for alkylation of said anthranilic amide compound of formula (Va) is selected from the group of alkyl halides, alkyl sulphates such as methyl-sulphate, alkyl peroxides, alkylsilyl peroxides, trialkyl phosphates, alkyl aldehydes (via reductive N-alkylation), halomethyl dialkylsilyl halogenides, metal complexes or triethyloxonium tetrafluoroborate. Optionally, the alkylation reaction can be carried out by a reductive amination/alkylation process or by any other means being state of the art.

Non limiting examples of alkyl halides used for the alkylation are selected from alkyl chlorides, alkyl bromides, alkyl iodides, alkyl fluorides or mixtures thereof. In one embodiment the alkyl halide is selected from the group consisting of alkyl chlorides, alkyl bromides, alkyl iodides and mixtures thereof. Preferably, the alkyl halide is an alkyl iodide selected from methyl iodide, ethyl iodide or propyl iodide.

In another embodiment, said anthranilic amide compound of formula (Va) is converted into a N-substituted anthranilic amide compound of formula (VI) by using suitable transamidation processes known in the prior art; for instance, by using transamidation processes as disclosed in *J. Am. Chem. Soc.*, 2006, 128 (50), pp 16406-16409; *Advanced Synthesis & Catalysis*, 2017, 359(2), pp 302-313; *RSC Adv.*, 2016, 6, pp 52724-52728 and *chemical papers*, 2015, 69 (11) 1421-1437.

In yet another embodiment, the anthranilic acid compound of formula (V) is converted into N-substituted anthranilic amide compound of formula (VI) by reacting said anthranilic acid compound of formula (V) with a suitable neuclophilic amine of formula $HN(R^{3a})(R^{3b})$, wherein $R^{3a}$ and $R^{3b}$ are independently hydrogen, $C_1$-$C_4$ alkyl or $C_3$-$C_6$ cycloalkyl-$C_1$-$C_4$ alkyl, in presence of a suitable coupling reagent.

In a preferred embodiment, the suitable coupling reagent is selected from but is not limited to 1-(3-dimethylaminopropyl)-3-ethylcarbodiimide hydrochloride (EDC), dicyclohexylcarbodiimide (DCC), 1-cyclohexyl-3-(2-morpholmoethyl)carbodiimide, 1,3-di-tert-butylcarbodiimide, 1-(dimethylaminopropyl)-3-ethylcarbodiimide methiodide, 1-tert-butyl-3-(1ùphenylmethyl)-carbodiimide, 1,3-diisopropylcarbodiimide, bis-(diphenylmethyl)-carbodiimide, 1-tert-butyl-3-ethylcarbodiimide, 1-methyl-2-chloropyridinium iodide, 2-ethoxy-1-ethoxycarbonyl-1,2-dihydroquinoline (EEDQ), BOP-chloride and isobutyl chloroformate.

The hydrolysis reaction is carried out by reacting a mono- or dicyano substituted aniline compound of formula (IV) in a suitable solvent with a suitable base at a temperature within the range of 20° C. to 120° C. for a period of 8 to 18 h to obtain an anthranilic acid compound of formula (V) or an anthranilic amide compound of formula (Va).

The suitable base useful for converting a mono- or di-cyano substituted aniline compound of formula (IV) to an anthranilic acid compound of formula (V) or to an anthranilic amide compound of formula (Va) includes but is not limited to inorganic or organic bases. An inorganic base is preferably selected from the group comprising of ammonia, alkali or alkaline earth metal hydroxide, carbonate, bicarbonate and the like, wherein the alkali and alkaline earth metal is selected from the group comprising of lithium, sodium, potassium, rubidium, caesium, calcium, magnesium, barium and the like or of mixtures thereof. The organic base is preferably selected form the group comprising of amines like methylamine, dimethyl amine, diethyl amine, triethylamine, diisopropylamine, diisopropyl ethyl amine, pyridine, alkylated and dialkylated pyridines, dimethylamino pyridine, piperidine, and the like or of mixtures thereof.

The suitable acid useful for converting a mono- or dicyano substituted aniline compound of formula (IV) to an anthranilic acid compound of formula (V) or to an anthranilic amide compound of formula (Va) includes but is not limited to may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like.

In one embodiment, the mono- or dicyano substituted aniline compound of formula (IV) is converted into a N-substituted anthranilic amide compound of formula (VI) by using the aminolysis of said mono- or dicyano substituted aniline compound of formula (IV) with suitable amine of formula $HN(R^{3a})(R^{3b})$, wherein $R^{3a}$ and $R^{3b}$ are independently selected from hydrogen, $C_1$-$C_4$ alkyl or $C_3$-$C_6$ cycloalkyl-$C_1$-$C_4$ alkyl.

In an embodiment, the cyanation reaction is carried out by reacting a mono-, di-, or tri-halogenated aniline compound of formula (III) with a suitable cyanation reagent by a classical nucleophilic substitution reaction or by a coupling reaction using a suitable metal catalyst, preferably a palladium catalyst and a suitable ligand at a temperature within the range of 80° C. to 170° C. for a period of 4 to 16 h to yield a mono- or dicyano substituted aniline compound of formula (IV).

The suitable metal catalyst is selected from but not limited to copper (0), copper (I) acetate, copper (I) bromide, copper (I) chloride, copper (I) iodide, copper (I) oxide, copper (II) trifluoromethanesulfonate, copper (II) acetate, copper (II) bromide, copper (II) chloride, copper (II) iodide, oxide of copper (II), NaX, KX, $CuX_2$, $MgX_2$, CsX or $ZnX_2$, wherein X is Cl, Br, I or F.

In another embodiment, the suitable metal catalyst is a palladium catalyst selected from, but is not limited to palladium (II) acetate, palladium chloride, palladium bromide, palladium iodide, dichlorobis (benzonitrile) palladium (II), dichlorobis (acetonitrile) palladium (II), palladium(II) (pi-cinnamyl) chloride dimer or the like; metallic palladium; palladium carbon; a zero-valent palladium such as bis (benzalacetone) palladium (0), tris (dibenzylideneacetone) dipalladium (0) or the like; a complex of a divalent to zero valent palladium with a ligand to be described later (for example, tetrakis (triphenylphosphine) palladium, bis (tri-tert-butylphosphine) palladium, bis (triphenylphosphine) palladium dichloride, 1,1'-bis(diphenylphosphino) ferrocene palladium dichloride, 1,1'-bis (diphenylphosphino) ferrocene palladium dichloride-dichloromethane complex, 1,2-bis (diphenylphosphino) ethane palladium dichloride), or the like.

The suitable ligand used is selected from, but is not limited to alkylphosphine ligand such as trimethylphosphine, triethylphosphine, tri-n-butylphosphine, di-tert-butylmethylphosphine, tri-tert-butylphosphine, tricyclohexylphosphine, butyl-di-1-adamantylphosphine, benzyl-di-1-adamantylphosphine, or the like; an alkylphosphonium ligand such as tri-n-butylphosphonium tetrafluoroborate, tri-tert-butylphosphonium tetrafluoroborate, di-tert-butylmethylphosphonium tetrafluoroborate, tricyclohexylphosphonium tetrafluoroborate, or the like; an arylphosphine ligand such as triphenylphosphine, tri-o-tolylphosphine, tri-p-tolylphosphine, tri (2-furyl)phosphine, tri (2-thienyl)phosphine, or the like; a bidentate phosphine ligand such as 1,2-bis (diphenylphosphino) ethane, 1,2-bis (diphenylphosphino) propane, 1,2-bis (diphenylphosphino) butane, α, α'-bis (di-tert-butylphosphino)-o-xylene, or the like; a ferrocene type phosphine ligand such as 1,1'-bis (diphenylphosphino) ferrocene, 1,1'-bis (di-tert-butylphosphino) ferrocene, 1,1'-bis(diisopropylphosphino) ferrocene, 1,2,3,4,5-pentaphenyl-1'-(di-tert-butylphosphino) ferrocene, or the like; a biaryl type phosphine ligand such as 2,2'-bis (diphenylphosphino)-1,1'-binaphthyl, 2,2'-bis (di-p-tolylphosphino)-1, V-binaphthyl, 2,'-bis[di(3,5-xylyl)phosphino]-1, 1'-binaphthyl, 2,2'-bis (diphenylphosphino)-1,1'-biphenyl, 2-di-tert-butylphosphino-1,1'-binaphthyl, 2-(di-tert-butylphosphino)-1,1'-biphenyl, 2-di-tert-butylphosphino-2'-(N,N-dimethylamino) biphenyl, 2-di-tert-butylphosphino-2'-methylbiphenyl, 2-(dicyclohexylphosphino) biphenyl, 2-(dicyclohexylphosphino)-2,6'-dimethoxy-1,1'-biphenyl, 2-(dicyclohexylphosphino)-2'-(N,N-dimethylamino)biphenyl, 2-(dicyclohexylphosphino)-2'-methylbiphenyl, 2-(dicyclohexylphosphino)-2',4',6'-tri-isopropyl-1,1'-biphenyl, 2-(diphenylphosphino)-2'-(N,N-dimethylamino) biphenyl, or the like; a pyrrole type phosphine ligand such as N-phenyl-2-(di-tert-butylphosphino) pyrrole, N-phenyl-2-(dicyclohexylphosphino) pyrrole, or the like; a diphenyl ether type phosphine ligand such as 9,9-dimethyl-4,5-bis (diphenylphosphino) xanthene, bis (2-diphenylphosphinophenyl) ether, or the like; a carbene ligand such as 1,3-bis (2,6-diisopropylphenyl)-4,5-dihydroimidazolium tetrafluoroborate, 1,3-bis (2, β-diisopropylphenyl)-4,5-dihydroimidazolium chloride, 1,3-bis (2,4,6-trimethylphenyl)-4,5-dihydroimidazolium chloride or the like.

In a preferred embodiment, the cyanation reaction is carried out by reacting a mono-, di-, or tri-halogenated aniline compound of formula (III) in a suitable solvent with a suitable cyanation reagent at a temperature in the range of 110° C. to 170° C. for a period of 4 to 8 h to give a mono- or dicyano substituted aniline compound of formula (IV).

The said suitable cyanation reagent useful for converting the mono-, di-, or tri-halogenated aniline compound of formula (III) to the mono- or dicyano substituted aniline compound of formula (IV) includes, but is not limited to, alkali metal cyanides, tert-butyl isocyanide, ethyl cyanoacetate, 2-chlorobenzyl thiocyanate, benzyl thiocyanate, dimethylmalononitrile, p-toluenesulfonylmethyl isocyanide, trimethylsilyl cyanide, cyanohydrin, acetone cyanohydrin, diethyl cyanophosphonate, 1-cyano-4-(dimethylamino)-pyridinium tetrafluoroborate and alkali metal hexacyanoferrates (II). Preferably, the metal cyanide reagent is selected from sodium cyanide, cuprous cyanide, zinc cyanide, nickel cyanide, iron (III) cyanide, potassium cyanide, acetone cyanohydrin, sodium hexacyanoferrate (II) and potassium hexacyanoferrate (II). More preferably, the metal cyanide reagent is selected from sodium cyanide or cuprous cyanide.

The halogenation reaction is carried out by reacting the substituted aniline compound of formula (II) in a suitable solvent with bromine, chlorine or iodine in the presence or absence of sodium bromide or calcium bromide at a temperature in the range of 0° C. to 50° C. for a period of 30 min to 2 h to afford mono-, di-, or tri-halogenated aniline compound of formula (III).

The halogenation as described in the present invention are carried out in the presence of a suitable halogenating reagent which includes, but is not limited to, HX, NaX, KX, CuX$_2$, MgX$_2$, CsX, ZnX$_2$, SOCl$_2$, SO$_2$Cl$_2$, COCl$_2$, X$_2$, C(=O)(OCl$_3$)$_2$, t-BuOCl, NaOCl, Chloramine-T, N-halosuccinamides, PDX$_3$, PX$_3$, PX$_5$ or metal halides; wherein X is Cl, Br, I or F.

The suitable solvents as used in any of the process steps of the present invention are selected from aliphatic, alicyclic or aromatic halogenated hydrocarbons such as chlorobenzene, dichlorobenzene, dichloromethane, chloroform, tetrachloromethane, dichloroethane or trichloroethane; ethers such as diethylether, diisopropyl ether, methyl tert-butyl ether, methyl tert-amyl ether, dioxane, tetrahydrofuran, 1,2-dimethoxy ethane, 1,2-diethoxyethane or anisole; nitriles such as acetonitrile, propionitrile, n- or iso-butyronitrile or benzonitrile; amides such as N,N-dimethylformamide, N,N-dimethylacetamide, N-methyl formanilide, N-methylpyrrolidone or hexamethylphosphoric triamide; sulfoxides such as dimethyl sulfoxide or sulfones such as sulfolane; alcohols such as methanol, ethanol, isopropanol, polyethylene glycols; water or mixtures thereof.

In one embodiment, the anthranilic acid compound of formula (V) or the anthranilic amide compound of formula (Va) may be isolated.

In another embodiment of the present invention, the anthranilic acid compound of formula (V) is reacted with a compound of formula (VII) to obtain a compound of formula (VIII) which is then reacted with an amine to obtain the anthranilic diamide compound of formula (I).

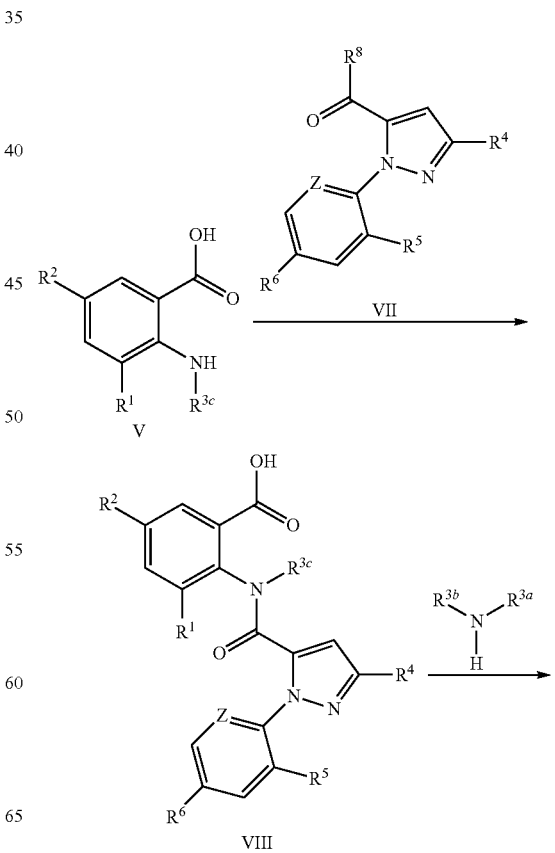

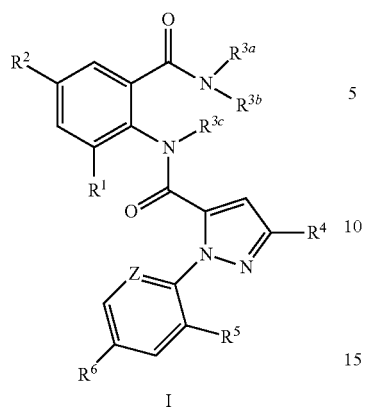

I wherein, $R^1$, $R^2$, $R^{3a}$, $R^{3b}$, $R^{3c}$, $R^4$, $R^5$, $R^6$, $R^8$ and Z are as defined herein above.

In another embodiment of the present invention, the present invention provides a process for the synthesis of N-substituted anthranilic acid compound of formula (VI),

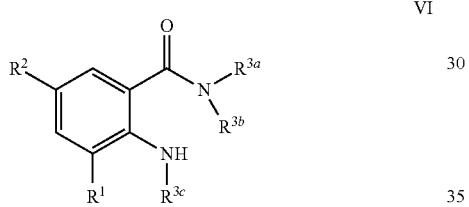

VI wherein, $R^1$, $R^2$, $R^{3a}$ and $R^{3b}$ are as defined above, comprising the steps of:

a) converting an anthranilic amide compound of formula (Va) into a N-substituted anthranilic amide compound of formula (VI) by either of the following steps:
  iii. in the presence of a suitable base or a suitable acid and a suitable alkylating reagent,
  iv. by using suitable transamidation process, according to the reaction scheme as depicted below:

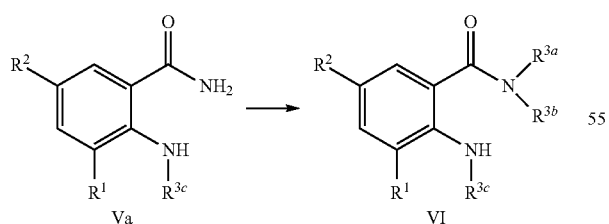

or
converting an anthranilic acid compound of formula (V) into a N-substituted anthranilic amide compound of formula (VI) using a suitable amine of formula $HN(R^{3a})(R^{3b})$ and a suitable coupling reagent, according to the reaction scheme as depicted below:

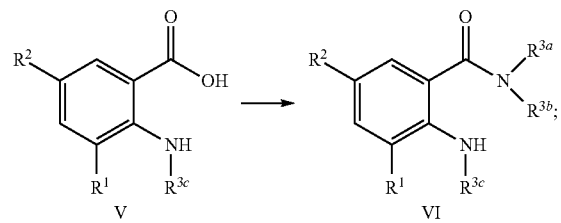

b) converting a mono- or dicyano substituted aniline compound of formula (IV) into the anthranilic acid compound of formula (V) or the anthranilic amide compound of formula (Va) optionally in the presence of a suitable base or a suitable acid, according to the reaction scheme as depicted below:

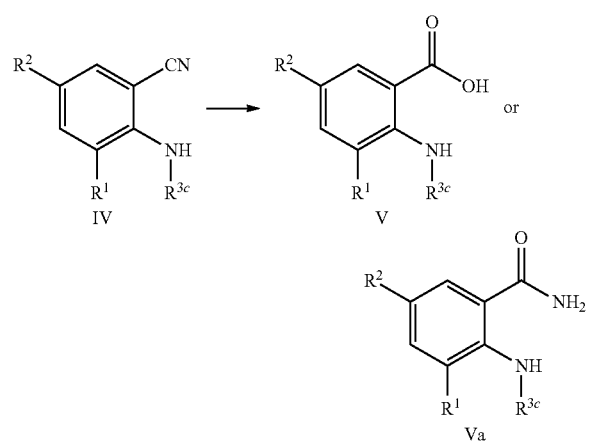

or
converting a mono- or dicyano substituted aniline compound of formula (IV) into the N-substituted anthranilic amide compound of formula (VI) by either of the following reaction steps:
  i) in the presence of a suitable base or a suitable acid and a suitable alkylating reagent,
  ii) aminolysis using a suitable amine of formula $HN(R^{3a})(R^{3b})$ according to the reaction scheme as depicted below:

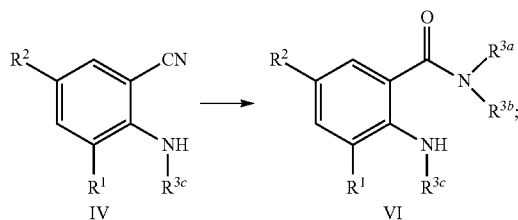

c) optionally, halogenating a mono- or dicyano substituted aniline compound of formula (IV), wherein $R^1$ and/or $R^2$ are hydrogen in the presence of a suitable halogenating agent to obtain a mono- or dicyano substituted aniline compound of formula (IV), wherein $R^1$ and/or $R^2$ are halogen;

d) converting a mono-, di-, or tri-halogenated aniline compound of formula (III) wherein X is halogen, into the mono- or dicyano substituted aniline compound of formula (IV) using a suitable cyanation reagent, according to the reaction scheme as depicted below:

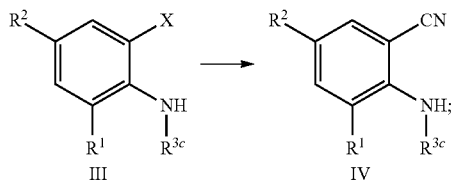

e) converting a substituted aniline compound of formula (II) into the mono-, di-, or tri-halogenated aniline compound of formula (III) wherein X is halogen, using a suitable halogenating agent, according to the reaction scheme as depicted below:

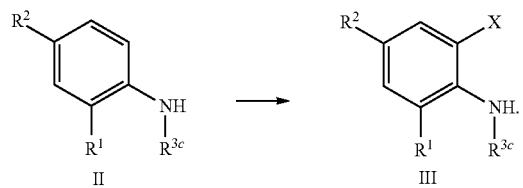

In yet another embodiment, the present invention provides a process for the synthesis of an anthranilic acid compound of formula (V) or an anthranilic amide compound of formula (Va),

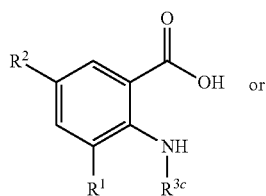

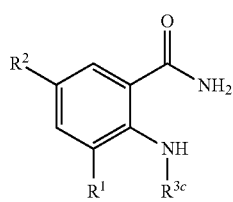

wherein $R^1$, $R^2$, $R^{3a}$ and $R^{3b}$ are as defined above, comprising the steps of:

a) converting a mono- or dicyano substituted aniline compound of formula (IV) into an anthranilic acid compound of formula (V) or an anthranilic amide compound of formula (Va) optionally in the presence of a suitable base or a suitable acid, according to the reaction scheme as depicted below:

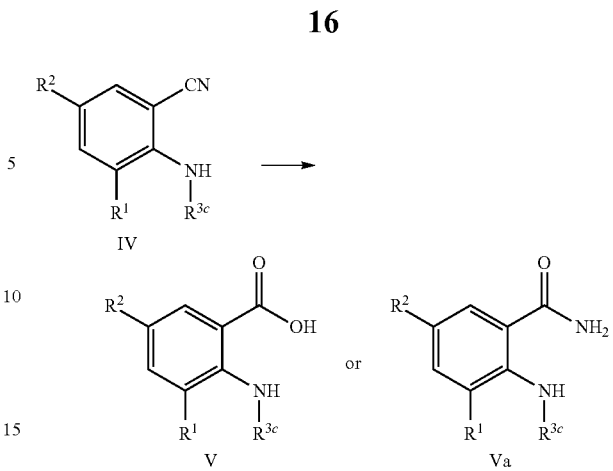

or converting a mono- or dicyano substituted aniline compound of formula (IV) into a N-substituted anthranilic amide compound of formula (VI) by either of the following reaction steps:
  i) in the presence of a suitable base or a suitable acid and a suitable alkylating reagent,
  ii) aminolysis using a suitable amine of formula $HN(R^{3a})(R^{3b})$, according to the reaction scheme as depicted below:

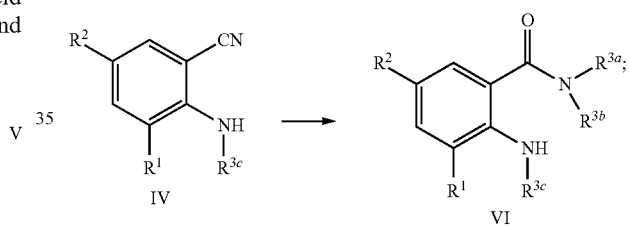

b) optionally, halogenating a mono- or dicyano substituted aniline compound of formula (IV), wherein $R^1$ and/or $R^2$ are hydrogen in the presence of a suitable halogenating agent to obtain a mono- or dicyano substituted aniline compound of formula (IV), wherein $R^1$ and/or $R^2$ are halogen;

c) converting a mono-, di-, or tri-halogenated aniline compound of formula (III) wherein X is halogen, into the mono- or dicyano substituted aniline compound of formula (IV) using a suitable cyanation reagent, according to the reaction scheme as depicted below:

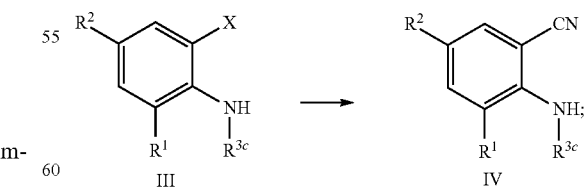

d) converting a substituted aniline compound of formula (II) into the mono-, di-, or tri-halogenated aniline compound of formula (III) wherein X is halogen, using a suitable halogenating agent, according to the reaction scheme as depicted below:

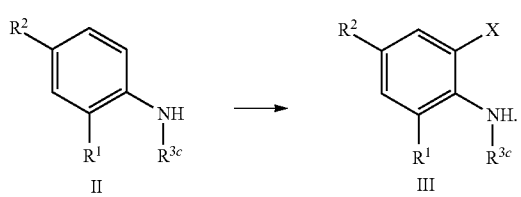

In yet another embodiment, the present invention provides a process for converting a mono-, di-, or tri-halogenated aniline compound of formula (III) wherein X is Cl, into the mono- or dicyano substituted aniline compound of formula (IV) using a suitable cyanation reagent and a suitable metal catalyst, according to the reaction scheme as depicted below,

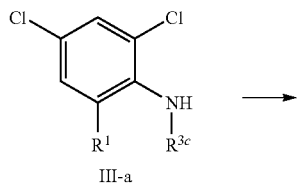

In yet another embodiment, the present invention provides a process for converting a dicyano substituted aniline compound of formula (IV-a) to an anthranilic acid compound of formula (V-a) or to an anthranilic amide compound of formula (V-aa) or to a compound of formula (VI-a) by using a suitable reagent such as suitable alkylating reagent or a suitable amine, according to the reaction scheme as depicted below,

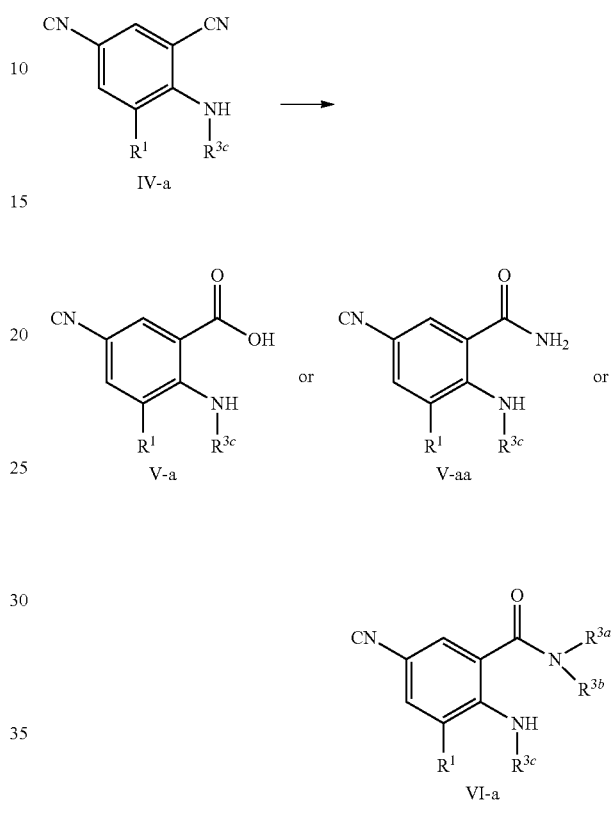

The process for the synthesis of anthranilic diamide compound of formula (I) as disclosed in the present invention is as depicted in scheme 1 below:

Scheme 1

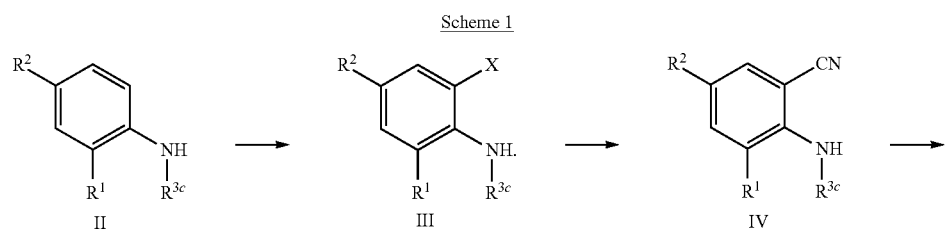

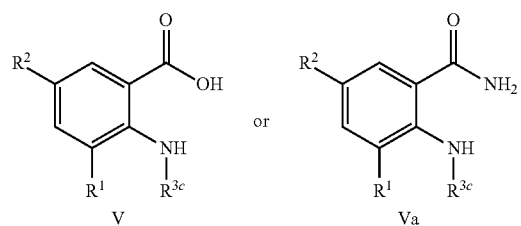

-continued

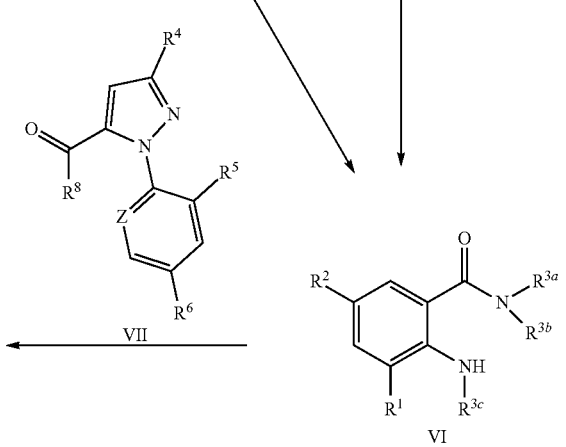

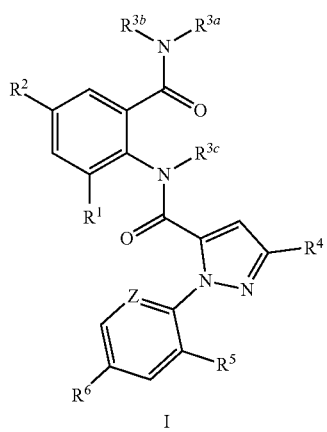

wherein, $R^1$, $R^2$, $R^{3a}$, $R^{3b}$, $R^{3c}$, $R^4$, $R^5$, $R^6$, $R^7$, $R^8$ and Z are as defined above.

In preferred embodiment, the present invention provides a process for preparing anthranilic diamide of formula I

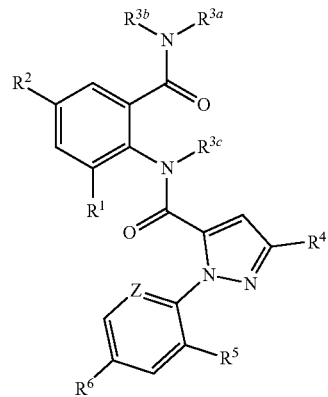

wherein,
$R^1$ is $CH_3$, Br or Cl;
$R^2$ is CN, Br or Cl;
$R^{3a}$ is H and $R^{3b}$ is methyl or 1-cyclopropyl ethyl;
$R^{3c}$ is H;
$R^4$ is Br or

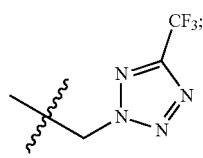

$R^5$ is Cl;
$R^6$ is H or Cl; and
Z is N.

In another embodiment, the present invention provides a process for preparing compound of formula VI

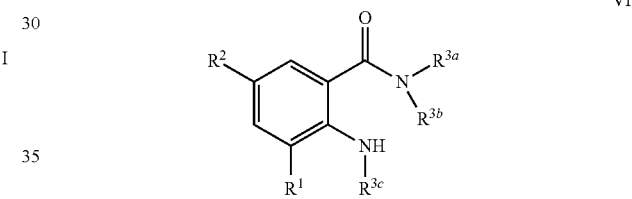

wherein,
$R^1$ is $CH_3$, Br or Cl;
$R^2$ is CN, Br or Cl;
$R^{3a}$ is H and $R^{3b}$ is methyl or 1-cyclopropyl ethyl;
$R^{3c}$ is H.

The processes as disclosed in the present invention are preferably carried out batch-wise. However, continuous reaction passages are also possible.

The processes as disclosed in the present invention can be run in the absence of a solvent or in the presence of one or more suitable solvent. The optional solvent should be resistant against oxidation (i.e. a solvent will be preferred whose rate of oxidation is substantially slower than that of the compounds of formula I to VII) and suitable for suspending, or preferably dissolving the reactants.

Any person skilled in the art knows the best work-up of the reaction mixtures after the end of the respective reactions. In one embodiment, the work-up is usually carried out by isolation of the product by filtration, and optionally washing with solvent, further optionally drying of the product if required.

The process steps according to the invention are generally carried out under atmospheric pressure. Alternatively, however, it is also possible to work in a vacuum or under pressure.

Without further elaboration, it is believed that any person skilled in the art who is using the preceding description can utilize the present invention to its fullest extent. The following examples are therefore to be interpreted as merely illustrative and not limiting of the disclosure in any way whatever.

EXAMPLES

The compound of formula (V) can be converted to a compound of formula (VI) by using any of the method known in the prior art and as disclosed in these prior art documents CN106146414A, WO2016131098, *ACS Med. Chem. Lett.,* 2017, 8 (6), pp 678-681 and *Chem. Commun.,* 2018, 54, 12766-12769.

The compound of formula (VI) is converted to a compound of formula (I) by using any of the method known in the prior art and as disclosed in the PCT patent applications WO2012103436, WO2008010897 and WO2006062978.

Example 1: Synthesis of 2-amino-3-bromo-5-chlorobenzoic acid

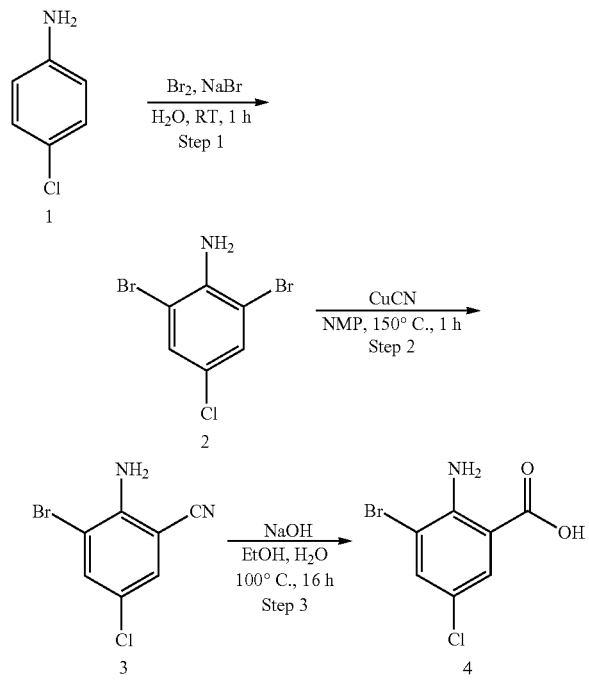

a) Step-1: Synthesis of 2,6-dibromo-4-chloroaniline

To a stirred solution of sodium bromide (1.7 g, 16.5 mmol) in water (10 mL), bromine (0.9 ml, 16.5 mmol) was added at 25° C. The resulting solution was added drop wise to 4-chloroaniline (1 g, 7.8 mmol) at 25° C. After completion of the reaction, the reaction mixture was filtered, the obtained solid was washed successively with water (50 mL) and 10% aqueous sodium thiosulphate solution (20 mL) and dried under reduced pressure to obtain 2,6-dibromo-4-chloroaniline (2.2 g, 7.9 mmol, 100% yield). $^1$H-NMR (400 MHz, DMSO-d$_6$) δ 7.54 (s, 2H), 5.49 (s, 2H).

b) Step-2: Synthesis of 2-Amino-3-Bromo-5-Chlorobenzonitrile

To a stirred solution of 2,6-dibromo-4-chloroaniline (1.0 g, 3.5 mmol) in N-methyl pyrrolidinone (1.6 mL), cuprous cyanide (0.3 g, 3.8 mmol) was added and the reaction mixture was stirred at 150° C. for 1 h. After completion of the reaction, the reaction mixture was diluted with a mixture of ethyl acetate (10 mL) and water (10 mL) and filtered through celite bed. The obtained filtrate was diluted with ice water (10 mL) and extracted twice with ethyl acetate (20 mL). The combined ethyl acetate layers were dried over anhydrous sodium sulphate and concentrated under reduced pressure. The crude product was purified by flash chromatography using ethyl acetate and hexane as eluent to obtain 2-amino-3-bromo-5-chlorobenzonitrile (0.52 g, 2.2 mmol, 64% yield). $^1$H-NMR (400 MHz, CHLOROFORM-D) δ 7.81 (d, J=2.4 Hz, 1H), 7.68 (d, J=2.4 Hz, 1H), 6.26 (s, 2H).

c) Step-3: Synthesis of 2-amino-3-bromo-5-chlorobenzoic Acid

A solution of 2-amino-3-bromo-5-chlorobenzonitrile (0.2 g, 0.9 mmol) in ethanol (2 mL) was added to an aqueous solution of sodium hydroxide (0.1 g, 2.6 mmol) and stirred for 16 h at 100° C. After completion of the reaction, the volatiles were removed from the reaction mixture and the reaction mixture was diluted with water, acidified to pH 3.0 using 2 M aqueous hydrochloric acid. The precipitated material was filtered and dried to obtain 2-amino-3-bromo-5-chlorobenzoic acid (160 mg, 0.6 mmol, 74% yield). $^1$H-NMR (400 MHz, DMSO-d$_6$) δ 13.33 (bs, 1H), 7.75 (d, J=2.4 Hz, 1H), 7.72 (d, J=2.4 Hz, 1H), 6.83 (s, 2H), LCMS: [249.85]$^{M-H}$.

Example 2: Synthesis of 2-amino-5-cyano-N,3-dimethylbenzamide

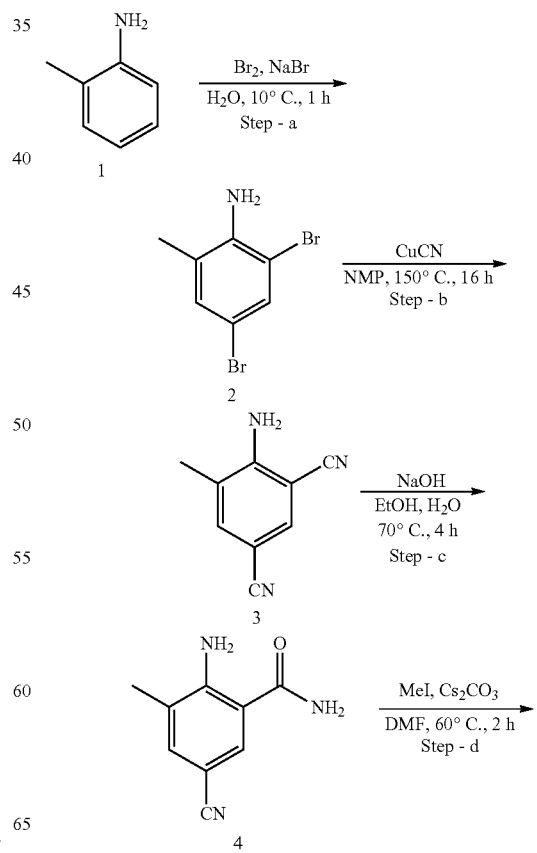

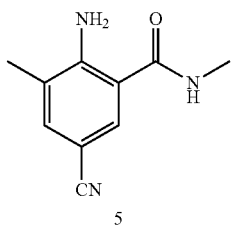

a) Step-1: Synthesis of 2,4-dibromo-6-methylaniline

To a solution of sodium bromide (19.2 g, 187 mmol) in water (50 mL), bromine was added at 25° C. The resultant solution was added drop wise to o-toluidine (10.3 ml, 93 mmol) at 10° C. The reaction mixture was stirred for 30 min at 10° C. After completion of the reaction, the reaction mixture was diluted with water (50 mL), filtered, the obtained solid was washed successively with water and 10% aqueous sodium thiosulphate solution and dried under reduced pressure to obtain 2,4-dibromo-6-methylaniline (23 g, 87 mmol, 93% yield). $^1$H-NMR (400 MHz, DMSO-$d_6$) δ 7.44-7.34 (1H), 7.20-7.11 (1H), 4.46-4.20 (bs, 2H).

b) Step-2: Synthesis of 4-amino-5-methylisophthalonitrile i) To a stirred solution of 2,4-dibromo-6-methylaniline (20 g, 75 mmol) in N-methyl pyrrolidinone (60 mL), cuprous cyanide (20 g, 151 mmol) was added and the reaction mixture was stirred at 150° C. for 6 h. After completion of the reaction, the reaction mixture was diluted with a mixture of 30% aqueous ammonium hydroxide solution (50 mL) and ethyl acetate (100 mL) and stirred for 1 h. The layers were separated and aqueous layer was extracted with ethyl acetate. The combined ethyl acetate layers were washed successively with water (50 mL) and brine solution (50 mL). The ethyl acetate layer was dried over anhydrous sodium sulphate and concentrated under reduced pressure to obtain 4-amino-5-methylisophthalonitrile (8.7 g, 55.4 mmol, 73% yield). LCMS: $[1561]^{M-H}$, $^1$H-NMR (400 MHz, DMSO-$d_6$) δ 7.87 (d, J=1.8 Hz, 1H), 7.56 (d, J=0.9 Hz, 1H), 6.75 (s, 2H), 2.10 (s, 3H).

ii) To a stirred mixture of 2,4-dibromo-6-methylaniline (1.0 g, 3.77 mmol), potassium iodide (0.25 g, 1.510 mmol), copper(I) iodide (0.14 g, 0.755 mmol), and potassium ferricyanide (1.243 g, 3.77 mmol) in polyethylene glycol (PEG) (10 mL), a solution of sym-dimethylethylenediamine (1.016 ml, 9.44 mmol) in polyethylene glycol (PEG) (5 mL) was added under nitrogen atmosphere. The reaction mixture was heated at 175° C. for 4 h. After completion of the reaction, the reaction mixture was diluted in ethyl acetate (80 mL), washed with water (2×70 mL) and saturated solution of ammonium chloride (3×70 mL). The combined ethyl acetate layers were dried over sodium sulfate, concentrated under reduced pressure to the crude product which was crystalized in ethanol to obtain pure product 4-amino-5-methylisophthalonitrile (350 mg, 2.227 mmol, yield 67%).

iii) The reaction mixture of 2,4-dibromo-6-methylaniline (50 g, 189 mmol), N,N-dimethylformamide (100 mL), potassium ferrocyanide (27.8 g, 75 mmol), sodium carbonate (20 g, 189 mmol), 2-dicyclohexylphosphino-2',4',6'-tri-iso-propyl-1,1'-biphenyl (9 g, 18.87 mmol) and bis(dibenzylideneacetone)palladium (5.43 g, 9.44 mmol) was heated to 130° C. for 6 h. After completion of the reaction, the reaction mixture was allowed to cool to 25° C., filtered through celite bed and washed with dichloromethane. The filtrate was concentrated under reduced pressure to obtain crude product, which was then dissolved in dichloromethane, to this mixture tert-butylmethyl ether was added and the mixture was stirred at 25° C. for 2 h. The mixture was filtered, the solid residue was stirred in ethanol (30 mL) at 10-15° C. for 5 h and filtered to obtain pure product 17 g. Then both the filtrates were mixed together, concentrated and purified by flash column chromatography to obtain little impure second crop, which was again stirred in ethanol (7 mL) for 16 h to obtain pure product 6 g. (HPLC purity 89%), 4-amino-5-methylisophthalonitrile 23 g, 146 mmol, yield 78%). MS: m/z=156.00 [M−H]. $^1$H-NMR (400 MHz, CDCl$_3$) δ 7.85 (d, J=2.0 Hz, 1H), 7.53 (d, J=0.8 Hz, 1H), 6.73 (s, 2H), 2.07 (s, 3H).

iv) The reaction mixture of 2,4-dibromo-6-methylaniline (10 g, 37.7 mmol), potassium ferrocyanide (6.38 g, 15.10 mmol), palladium II acetate (1.729 g, 3.77 mmol) and sodium acetate (6.19 g, 75 mmol) in N,N-dimethylformamide (70 mL) was heated at 150° C. for 18 h. After the completion of reaction, the solvent was removed under reduced pressure; the crude product was diluted in ethyl acetate (500 mL), filtered through celite and washed with ethyl acetate and water (300 mL). The filtrate was washed with saturated solution of sodium bicarbonate (2×200 mL) and brine (2×200 mL), dried over sodium sulfate, concentrated to obtain crude compound (15 g). Ethanol (100 mL) was added to the crude compound and the mixture was stirred for 16 h. The mixture was cooled to 0° C. and filtered to obtain pure product 4-amino-5-methylisophthalonitrile (4.6 g; 29.3 mmol, yield 78%).

v) To a stirred mixture of 2,4-dibromo-6-methylaniline (0.600 g, 2.265 mmol), sodium cyanide (NaCN) (0.222 g, 4.53 mmol), copper (I) iodide (0.129 g, 0.679 mmol), potassium iodide (0.226 g, 1.359 mmol) in xylene (3 mL), a solution of sym-dimethylethylenediamine (0.600 g, 2.265 mmol) in xylene (0.5 mL) was added under nitrogen atmosphere. The reaction was heated at 175° C. for 16 h, then the mixture was diluted in ethyl acetate (70 mL) and water (75 mL), separated organic layer washed by sat. solution of ammonium chloride (50 mL), sat. solution of sodium bicarbonate (50 mL) and brine (50 mL). The organic layer was dried over sodium sulfate and concentrated to obtain crude material (0.685 g), which was purified by flash column chromatography to obtain pure product 4-amino-5-methylisophthalonitrile (0.085 g, 0.541 mmol, 24% yield).

vi) To a stirred solution of 2,4-dibromo-6-methylaniline (0.500 g, 1.887 mmol) in N-Methyl-2-pyrrolidinone (5 mL), copper (I) cyanide (0.340 g, 3.79 mmol) was added. The reaction mixture was stirred at 160° C. for 16 h. After completion of the reaction, the reaction mixture was diluted with 30% aqueous ammonia solution (50 mL) and ethyl acetate (300 mL), and further stirred for 1 h. The reaction mixture was extracted using ethyl acetate (50 mL), washed with water (30 mL), and brine (30 mL) evaporated to dryness to obtain desired product, purification in dichloromethane and diethyl ether to obtain 4-amino-5-methylisophthalonitrile (0.200 g, 1.272 mmol, 67% yield).

c) Step-3: Synthesis of 2-amino-5-cyano-3-methylbenzamide:

A reaction mixture of aqueous sodium hydroxide (0.5 g, 12.7 mmol) and 4-amino-5-methylisophthalonitrile (2g, 12.7 mmol) in ethanol (15 mL) was stirred at 70° C. for 4 h. After completion of the reaction, the reaction mixture was diluted with ice-water (30 mL) and the precipitate obtained was filtered, washed with water (20 mL) and dried under reduced pressure to obtain 2-amino-5-cyano-3-methylbenzamide (1.6 g, 9.13 mmol, 72% yield) as an off-white solid. $^1$H-NMR (400 MHz, DMSO-$d_6$) δ 7.97-7.90 (bs, 1H), 7.89-7.84 (m, 1H), 7.45-7.37 (m, 1H), 7.36-7.22 (bs, 3H), 2.08 (s, 3H), LCMS: $[363.8]^{M-H}$.

d) Step-4: 2-amino-5-cyano-N,3-dimethylbenzamide

To a mixture of 2-amino-5-cyano-3-methylbenzamide (200 mg, 1.1 mmol) and cesium carbonate (446 mg, 1.4 mmol) in dimethylformamide (2 mL), methyl iodide was added and the reaction mixture was stirred for 2 h at 60° C. in sealed tube. After completion of the reaction, the reaction mixture was diluted with ethyl acetate (20 mL) and washed twice with brine solution (20 mL). The ethyl acetate layer was dried over anhydrous sodium sulphate and concentrated under reduced pressure to obtain crude product, which was purified by flash chromatography using ethyl acetate and hexane as eluent to obtain 2-amino-5-cyano-N,3-dimethylbenzamide (86 mg, 0.5 mmol, 40% yield). $^1$H-NMR (400 MHz, DMSO-$d_6$) δ 8.50-8.35 (1H), 7.89-7.75 (1H), 7.51-7.37 (1H), 7.25-7.09 (2H), 2.79-2.68 (3H), 2.15-2.05 (3H), LCMS: $[463.8]^{M-H}$.

Example 3: Synthesis of
2-amino-3-bromo-5-chlorobenzonitrile

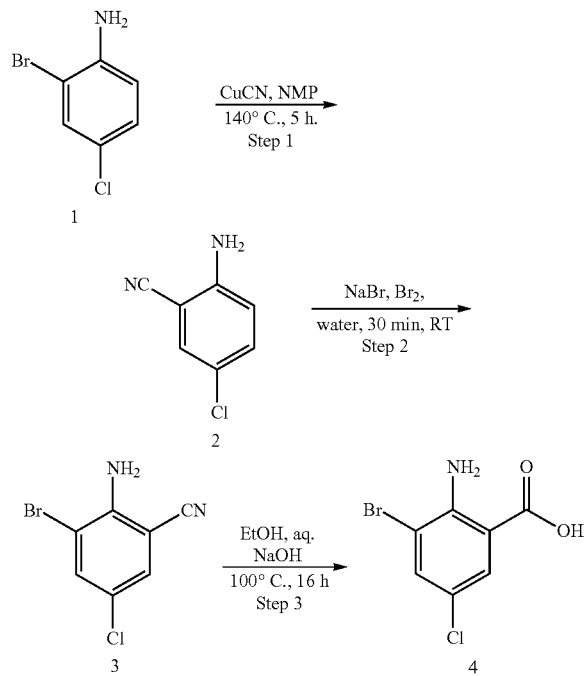

a) Step-1: Synthesis of
2-amino-5-chlorobenzonitrile

To a stirred solution of 2-bromo-4-chloroaniline (20 g, 97 mmol) in N-methyl-2-pyrrolidone (70 ml), was added cuprous cyanide (19.14 g, 145 mmol). The resultant reaction mixture was stirred at 140° C. for 5 h. After completion of the reaction, the reaction mixture was cooled to 25° C. and poured onto water (250 mL). The solid obtained was filtered and washed with water and aqueous sodium bicarbonate solution. The crude product was dissolved in ethyl acetate (100 mL) and washed subsequently with water (30 mL), aqueous ammonium hydroxide (30 mL) and brine solution (30 mL). The ethyl acetate layer was dried over anhydrous sodium sulphate and concentrated under reduced pressure. The concentrate was triturated with hexane and dried under reduced pressure to obtain 2-amino-5-chlorobenzonitrile (11.8 g, 77 mmol, 80% yield). $^1$HNMR (400 MHz, DMSO-$d_6$) δ 7.47 (d, J=2.4 Hz, 1H), 7.31 (dd, J=9.2, 2.4 Hz, 1H), 6.77-6.79 (m, 1H), 6.22 (s, 2H), GCMS: [206.9].

b) Step-2: Synthesis of
2-amino-3-bromo-5-chlorobenzonitrile

To a stirred solution of sodium bromide (0.7 g, 7.2 mmol) in water (10 mL), bromine (0.4 ml, 7.2 mmol) was added drop wise at 25° C. To this solution 2-amino-5-chlorobenzonitrile (1 g, 6.55 mmol) was added and stirred at 25° C. for 30 min. After completion of the reaction, the reaction mixture was filtered, washed with water and 10% aqueous sodium thiosulphate solution (20 mL) and dried under reduced pressure to obtain 2-amino-3-bromo-5-chlorobenzonitrile (1.4 g, 6.05 mmol, 92% yield). $^1$HNMR (400 MHz, DMSO-D6) δ 7.82 (d, J=2.4 Hz, 1H), 7.66 (d, J=2.4 Hz, 1H), 6.27 (s, 2H), GCMS: [231.8].

c) Step-3: Synthesis of 2-amino-3-bromo-5-chlorobenzonitrile

To a stirred suspension of 2-amino-3-bromo-5-chlorobenzonitrile (1.4 g, 6 mmol) in ethanol (8 mL), a solution of sodium hydroxide (0.7 g, 18.1 mmol) in water (8 mL) was added and stirred at 100° C. for 16 h. After completion of the reaction, the reaction mixture was concentrated under reduced pressure to obtain semi solid, which was diluted with water and acidified with 10% aqueous hydrochloric acid to obtain desired crude product as a solid, which was filtered and dried to obtain 2-amino-3-bromo-5-chlorobenzoic acid (1.48 g, 5.9 mmol, 98% yield). $^1$HNMR (400 MHz, DMSO-$d_6$) δ 13.28 (s, 1H), 7.74 (d, J=2.4 Hz, 1H), 7.72 (d, J=2.4 Hz, 1H), 6.77 (s, 2H), LCMS: $[249.85]^{M+2}$.

Example-4: Synthesis of
4-amino-5-methylisophthalonitrile i) To a mixture of 2,4-dichloro-6-methylaniline (2.0 g, 11.36 mmol), [(cinnamyl)PdCl]$_2$ (0.063 g, 0.11 mmol), 2-dicyclohexylphosphino-2',4',6'-tri-iso-propyl-1,1'-biphenyl (0.162 g, 0.34 mmol) and N,N-diisopropylethylamine (9.92 mL, 56.8 1 mmol), n-butanol (20 mL) was added under argon atmosphere. The reaction mixture was purged with argon for 10 min. Then the reaction mixture was heated at 80° C. followed by the addition of acetone cyanohydrin (2.079 mL, 22.72 mmol) diluted in n-butanol (20 mL) over a period of 3 h. After completion the reaction, the reaction mixture was cooled to 25° C., concentrated under reduced pressure to obtain the crude, which was then washed with ice cold water (20 mL), the obtained precipitate was filtered and dried to obtain 4-amino-5-methylisophthalonitrile (1.5 g, 9.54 mmol, 84% yield). $^1$H-NMR (400 MHz, DMSO-$d_6$) δ: 7.89 (d, J=1.7 Hz, 1H), 7.57 (d, J=1.7 Hz, 1H), 6.76 (s, 2H), 2.10 (s, 3 H). GCMS: 157.1.

ii) To a mixture of 2,4-dichloro-6-methylaniline (10 g, 56.8 mmol), [(cinnamyl)PdCl]$_2$ (0.31 g, 0.56 mmol), 2-dicyclohexylphosphino-T,4',6'-tri-iso-propyl-1,1'-biphenyl (0.81 g, 1.7 mmol), N,N-diisopropylethylamine (DIPEA) (49.6 mL, 284 mmol), n-butan-1-ol (100 mL) was added under argon atmosphere. The reaction mixture was purged with argon for 10 min. Then the reaction mixture was heated at 85° C. followed by the addition of acetone cyanohydrin (8.32 mL, 91 mmol) diluted in n-butanol (100 mL) over a period of 5 h. After completion of the reaction, the reaction mixture was cooled to 25° C., concentrated under reduced pressure to obtain the crude, that was purified with combi flash using 0-60% ethyl acetate in hexane as eluent to obtain 2-amino-5-chloro-3-methylbenzonitrile (2.6 g, 15.61 mmol, 27% yield) and 4-amino-5-methylisophthalonitrile (4.5 g, 28.6 mmol, 50% yield).

2-amino-5-chloro-3-methylbenzonitrile: $^1$H-NMR (400 MHz, DMSO-$d_6$) δ 7.39 (d, J=1.6 Hz, 1H), 7.27 (d, J=2.0 Hz, 1H), 5.93 (s, 2H), 2.11 (s, 3 H). GCMS: 166.1;

4-amino-5-methylisophthalonitrile: $^1$H-NMR (400 MHz, DMSO-$d_6$) δ: 7.89 (d, J=1.7 Hz, 1H), 7.57 (d, J=1.7 Hz, 1H), 6.76 (s, 2 H) 2.10 (s, 3 H). GCMS: 157.1.

iii) To a mixture of 2,4-dichloro-6-methylaniline (100 g, 568 mmol), [(cinnamyl)PdCl]$_2$ (1.57 g, 2.84 mmol), 2-dicyclohexylphosphino-2',4',6'-tri-iso-propyl-1,1'-biphenyl (1.57, 2.84 mmol) and N,N-diisopropylethylamine (DIPEA) (496 mL, 2.84 mol), n-butanol (1000 mL) was added under nitrogen atmosphere. Then the reaction mixture was purged with nitrogen for 10 min. The reaction mixture was heated to 85° C. followed by addition of acetone cyanohydrin (83 mL, 909 mmol) in n-butanol (500 mL) over a period of 5 h. After completion of the reaction, the reaction mixture was cooled to 25° C. The solvent was evaporated under reduced pressure to obtain the crude residue, which was then washed with ice cold water (2000 mL). The obtained solid was filtered and dried to obtain crude product. The obtained crude product was dissolved in hot ethanol (1000 mL), cooled, the solid precipitate was filtered, dried to obtain 4-amino-5-methylisophthalonitrile (28 g, 178 mmol, 31% yield), filtrate was concentrated under reduced pressure and again dissolved in hot ethanol (500 mL), cooled and filtered to obtain mixture of products as solid (20 g). The filtrate was concentrated to obtain 2-amino-5-chloro-3-methylbenzonitrile (37 g, 222 mmol, 39% yield).

2-amino-5-chloro-3-methylbenzonitrile: $^1$H-NMR (400 MHz, DMSO-$d_6$) δ: 7.39 (d, J=1.6 Hz, 1H), 7.27 (d, J=2.0 Hz, 1H), 5.93 (s, 2H), 2.11 (s, 3 H). GCMS: 166.1;

4-amino-5-methylisophthalonitrile: $^1$H-NMR (400 MHz, DMSO-$d_6$) δ: 7.89 (d, J=1.7 Hz, 1H), 7.57 (d, J=1.7 Hz, 1H), 6.76 (s, 2H), 2.10 (s, 3 H). GCMS: 157.1.

The invention claimed is:

1. A process for the synthesis of a compound of formula (I),

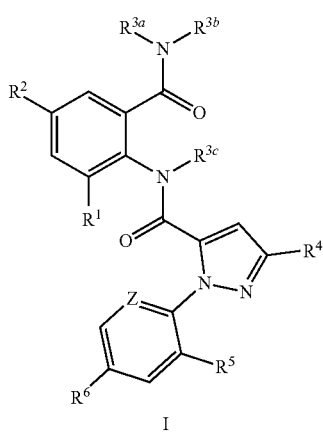

Formula (I)

wherein,
$R^1$ is $C_1$-$C_4$ alkyl or halogen;
$R^2$ is hydrogen, halogen or cyano;
$R^{3a}$ and $R^{3b}$ are independently hydrogen, $C_1$-$C_4$ alkyl or $C_3$-$C_6$ cycloalkyl-$C_1$-$C_4$ alkyl;
$R^{3c}$ are independently hydrogen or $C_1$-$C_4$ alkyl;
$R^4$ is halogen, $CF_3$, $OCF_2H$, $OCH_2CF_3$, or

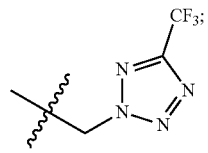 [SMILES: *Cn1nnc(C(F)(F)F)n1]

$R^5$ is halogen;
$R^6$ is hydrogen, halogen;
Z is $CR^7$ or N; and
$R^7$ is hydrogen or halogen,
comprising the steps of:
a) reacting a N-substituted anthranilic amide compound of formula (VI) with a pyrazole acid compound of formula (VII) to obtain the compound of formula (I),

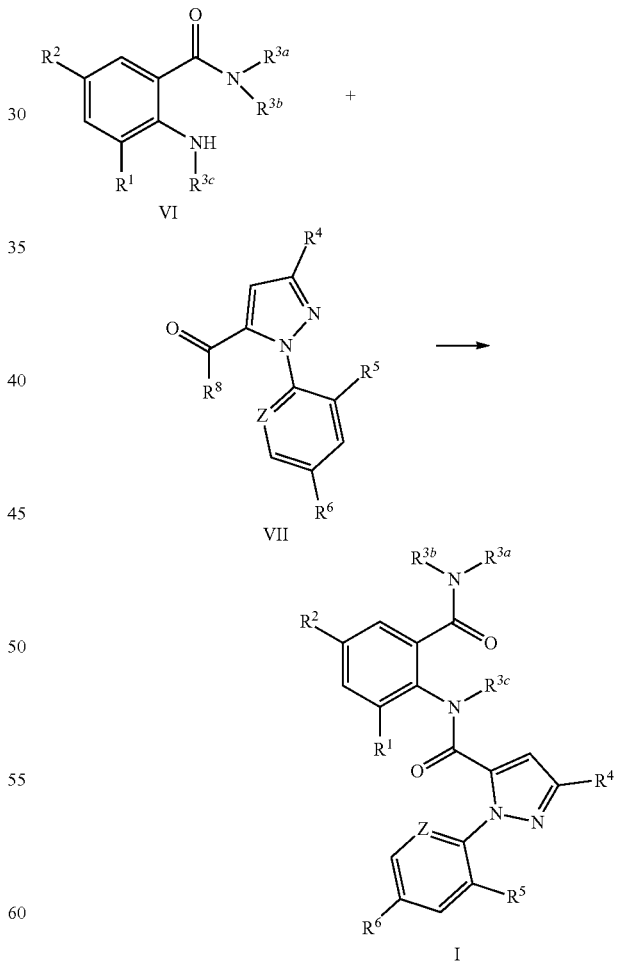

wherein, $R^8$ is OH, Cl, or O—$C_1$-$C_4$ alkyl;
b) converting an anthranilic amide compound of formula (Va) into the N-substituted anthranilic amide compound of formula (VI) by either of the following steps:

i. in the presence of a suitable base or a suitable acid and a suitable alkylating reagent, ii. by using suitable transamidation process, according to the reaction scheme as depicted below:

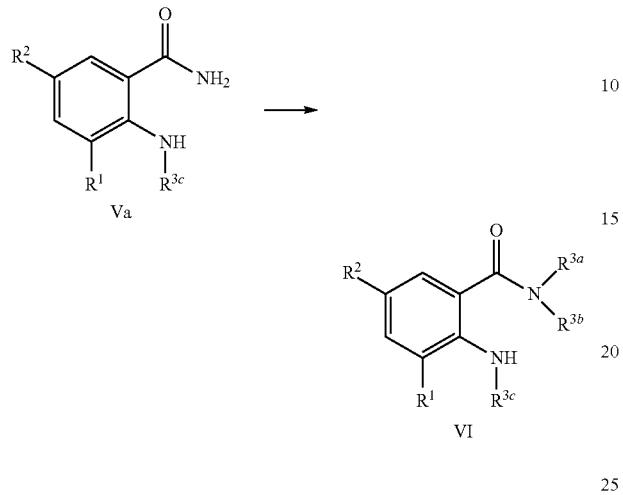

or converting an anthranilic acid compound of formula (V) into the N-substituted anthranilic amide compound of formula (VI) using a suitable amine of formula $HN(R^{3a})(R^{3b})$ and a suitable coupling agent according to the reaction scheme as depicted below:

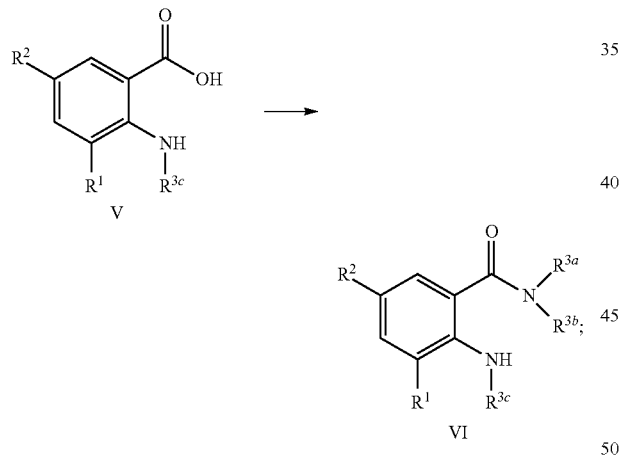

c) converting a mono- or dicyano substituted aniline compound of formula (IV) into the anthranilic acid compound of formula (V) or the anthranilic amide compound of formula (Va) optionally in the presence of a suitable base or a suitable acid according to the reaction scheme as depicted below:

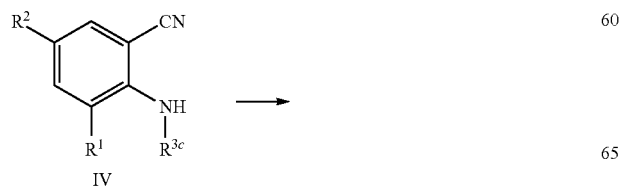

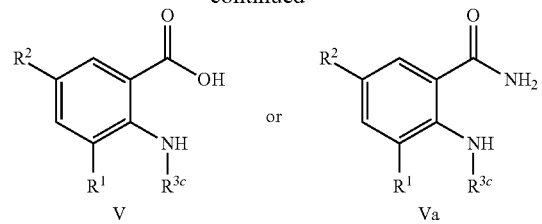

or converting a mono- or dicyano substituted aniline compound of formula (IV) into the N-substituted anthranilic amide compound of formula (VI) by either of the following reaction steps:

i) in the presence of a suitable base or a suitable acid and a suitable alkylating reagent, ii) aminolysis using a suitable amine of formula $HN(R^{3a})(R^{3b})$ according to the reaction scheme as depicted below:

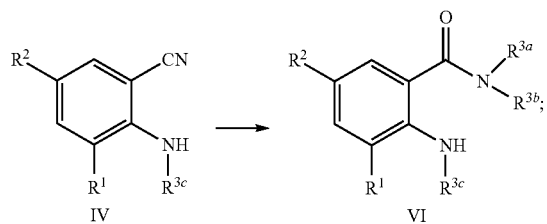

d) optionally, halogenating a mono- or dicyano substituted aniline compound of formula (IV), wherein $R^1$ and/or $R^2$ are hydrogen in the presence of a suitable halogenating agent to obtain a mono- or dicyano substituted aniline compound of formula (IV), wherein $R^1$ and/or $R^2$ are halogen;

e) converting a mono-, di-, or tri-halogenated aniline compound of formula (III) wherein X is halogen, into the mono- or dicyano substituted aniline compound of formula (IV) using a suitable cyanation reagent according to the reaction scheme as depicted below:

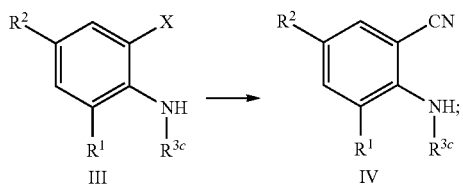

f) converting a substituted aniline compound of formula (II) into the mono-, di-, or tri-halogenated aniline compound of formula (III) wherein X is halogen, using a suitable halogenating agent, according to the reaction scheme as depicted below:

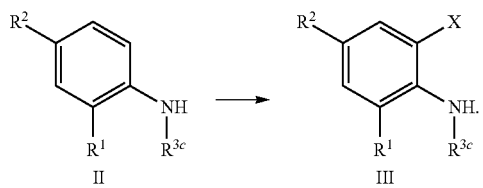
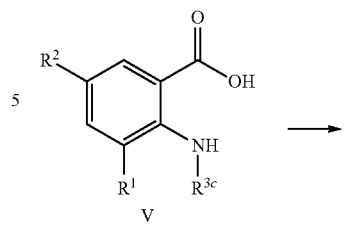

2. A process for the synthesis of a compound of formula (VI),

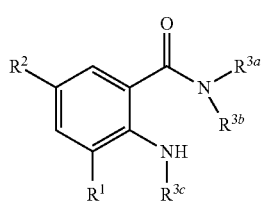

wherein,

R¹ is $C_1$-$C_4$ alkyl or halogen;

R² is hydrogen, halogen or cyano;

$R^{3a}$ and $R^{3b}$ are independently hydrogen, $C_1$-$C_4$ alkyl or $C_3$-$C_6$ cycloalkyl-$C_1$-$C_4$ alkyl;

$R^{3c}$ is hydrogen or $C_1$-$C_4$ alkyl;

comprising the steps of:

a) converting an anthranilic amide compound of formula (Va) into a N-substituted anthranilic amide compound of formula (VI) by either of the following steps:
  i. in the presence of a suitable base or a suitable acid and a suitable alkylating reagent,
  ii. by using suitable transamidation process, according to the reaction scheme as depicted below:

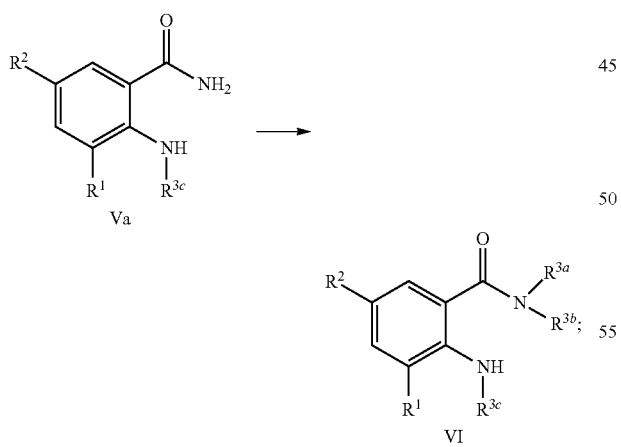

or converting an anthranilic acid compound of formula (V) into a N-substituted anthranilic amide compound of formula (VI) using a suitable amine of formula $HN(R^{3a})(R^{3b})$ and a suitable coupling reagent, according to the reaction scheme as depicted below:

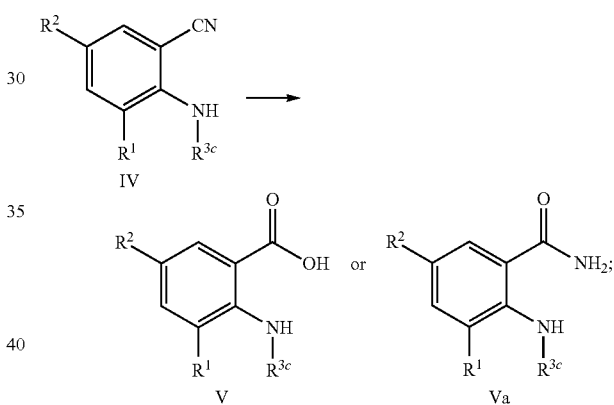

b) converting a mono- or dicyano substituted aniline compound of formula (IV) into the anthranilic acid compound of formula (V) or the anthranilic amide compound of formula (Va) optionally in the presence of a suitable base or a suitable acid, according to the reaction scheme as depicted below:

or converting a mono- or dicyano substituted aniline compound of formula (IV) into the N-substituted anthranilic amide compound of formula (VI) by either of the following reaction steps:
  i) in the presence of a suitable base or a suitable acid and a suitable alkylating reagent,
  ii) aminolysis using a suitable amine of formula $HN(R^{3a})(R^{3b})$ according to the reaction scheme as depicted below:

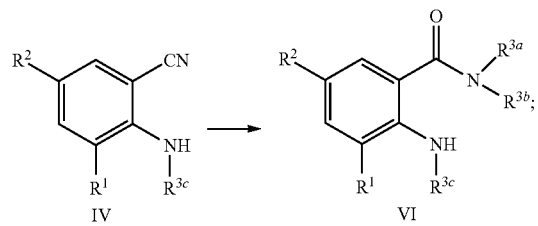

c) optionally, halogenating a mono- or dicyano substituted aniline compound of formula (IV), wherein R¹ and/or R² are hydrogen in the presence of a suitable halogenating agent to obtain a mono- or dicyano substituted aniline compound of formula (IV), wherein R¹ and/or R² are halogen;

d) converting a mono-, di-, or tri-halogenated aniline compound of formula (III) wherein X is halogen, into the mono- or dicyano substituted aniline compound of formula (IV) using a suitable cyanation reagent according to the reaction scheme as depicted below:

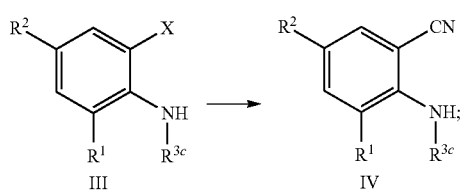

e) converting a substituted aniline compound of formula (II) into the mono-, di-, or tri-halogenated aniline compound of formula (III) wherein X is halogen, using a suitable halogenating agent, according to the reaction scheme as depicted below:

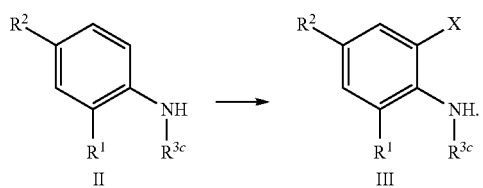

3. A process for the synthesis of an anthranilic acid compound of formula (V) or an anthranilic amide compound of formula (Va),

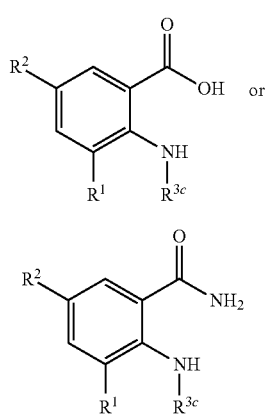

wherein,
R¹ is $C_1$-$C_4$ alkyl or halogen;
R² is hydrogen, halogen or cyano;
$R^{3c}$ is hydrogen or $C_1$-$C_4$ alkyl;
comprising the steps of:
a) converting a mono- or dicyano substituted aniline compound of formula (IV) into an anthranilic acid compound of formula (V) or an anthranilic amide compound of formula (Va) optionally in the presence of a suitable base or a suitable acid according to the reaction scheme as depicted below:

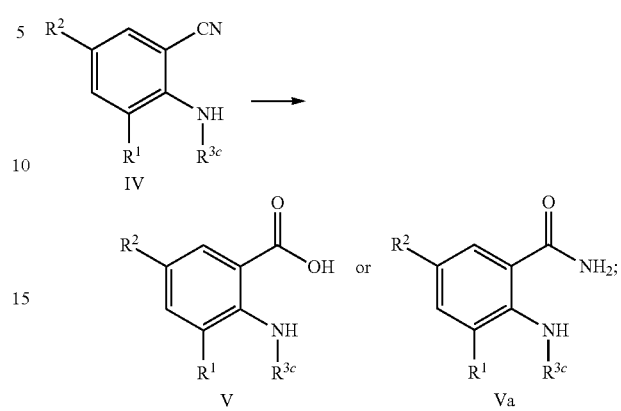

or
converting a mono- or dicyano substituted aniline compound of formula (IV) into a N-substituted anthranilic amide compound of formula (VI) by either of the following reaction steps:
i) in the presence of a suitable base or a suitable acid and a suitable alkylating reagent,
ii) aminolysis using a suitable amine of formula $HN(R^{3a})(R^{3b})$ according to the reaction scheme as depicted below:

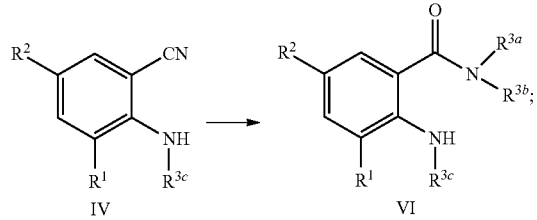

b) optionally, halogenating a mono- or dicyano substituted aniline compound of formula (IV), wherein R¹ and/or R² are hydrogen in the presence of a suitable halogenating agent to obtain a mono- or dicyano substituted aniline compound of formula (IV), wherein R¹ and/or R² are halogen;

c) converting a mono-, di-, or tri-halogenated aniline compound of formula (III) wherein X is halogen, into the mono- or dicyano substituted aniline compound of formula (IV) using a suitable cyanation reagent, according to the reaction scheme as depicted below:

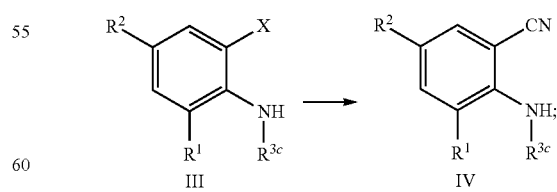

d) converting a substituted aniline compound of formula (II) into the mono-, di-, or tri-halogenated aniline compound of formula (III) wherein X is halogen, using a suitable halogenating agent, according to the reaction scheme as depicted below:

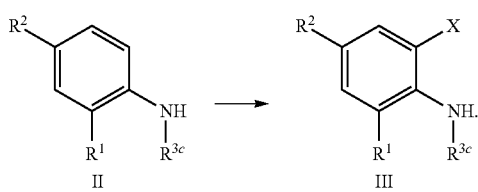

4. The process as claimed in claim 1, wherein said process comprises the conversion of a mono-, di-, or tri-halogenated aniline compound of formula (III) wherein X is Cl, into the mono- or dicyano substituted aniline compound of formula (IV) by using a suitable cyanation reagent, according to the reaction scheme as depicted below:

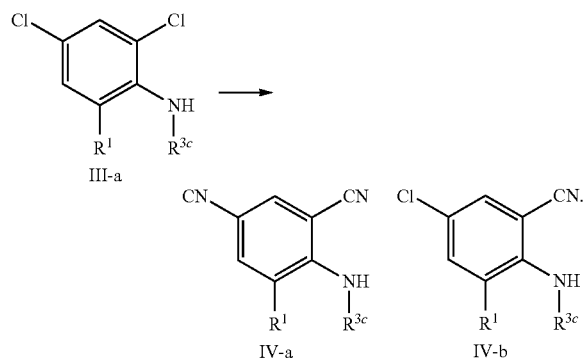

5. The process as claimed in claim 1, wherein said process comprises conversion of a dicyano substituted aniline compound of formula (IV-a) to an anthranilic acid compound of formula (V-a) or to an anthranilic amide compound of formula (V-aa) or to a compound of formula (VI-a) according to the reaction scheme as depicted below:

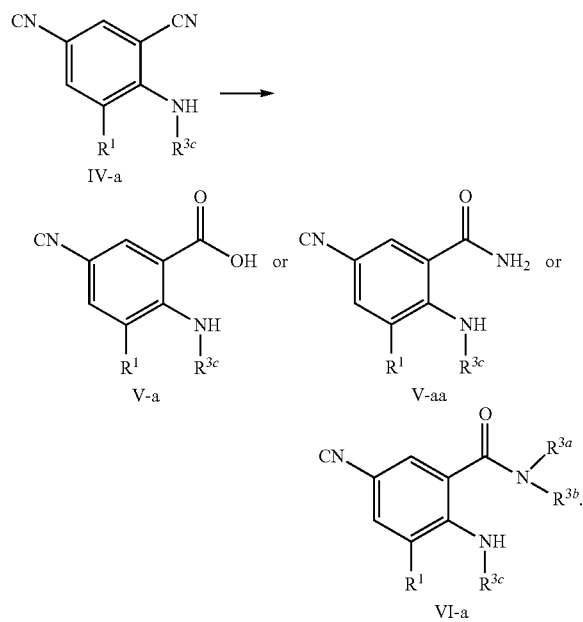

6. The process as claimed in claim 1, wherein said suitable cyanation reagent is selected from alkali metal cyanides, tert-butyl isocyanide, ethyl cyanoacetate, 2-chlorobenzyl thiocyanate, benzyl thiocyanate, dimethylmalononitrile, p-toluenesulfonylmethyl isocyanide, trimethylsilyl cyanide, cyanohydrin, acetone cyanohydrin, diethyl cyanophosphonate, 1-cyano-4-(dimethylamino)-pyridinium tetrafluoroborate or alkali metal hexacyanoferrates (II).

7. The process as claimed in claim 6, wherein said suitable cyanation reagent is selected from sodium cyanide, cuprous cyanide, zinc cyanide, nickel cyanide, iron (III) cyanide, potassium cyanide, sodium hexacyanoferrate (II) potassium hexacyanoferrate (II) and acetone cyanohydrin.

8. The process as claimed in claim 1, wherein said suitable halogenating reagent is selected from HX, NaX, KX, $CuX_2$, $MgX_2$, CsX, $ZnX_2$, $SOCl_2$, $SO_2Cl_2$, $COCl_2$, $X_2$, C(=O)$(OCl_3)_2$, t-BuOCl, NaOCl, chloramine-T, N-halosuccinamides, $PDX_3$, $PX_3$, $PX_5$ or metal halides; wherein X is Cl, Br, I or F.

9. The process as claimed in claim 1, wherein said suitable solvent is selected from chlorobenzene, dichlorobenzene, dichloromethane, chloroform, tetrachloromethane, dichloroethane, trichloroethane, diethylether, diisopropyl ether, methyl tert-butyl ether, methyl tert-amyl ether, dioxane, tetrahydrofuran, 1,2-dimethoxy ethane, 1,2-diethoxyethane, anisole, acetonitrile, propionitrile, n- or iso-butyronitrile, benzonitrile, N,N-dimethylformamide, N,N-dimethylacetamide, N-methylformanilide, N-methylpyrrolidone, hexamethylphosphoric triamide, dimethyl sulfoxide, sulfones, sulfolane, methanol, ethanol, isopropanol, water or mixtures thereof.

10. The process as claimed in claim 1, wherein said suitable alkylating agent is selected from the group of alkyl halides, alkyl sulphates, alkyl peroxides, alkylsilyl peroxides, trialkyl phosphates, alkyl aldehydes (via reductive N-alkylation), halomethyl dialkylsilyl halogenides, metal complexes or triethyloxonium tetrafluoroborate.

11. The process as claimed in claim 10, wherein said alkyl halides is selected from alkyl chlorides, alkyl bromides, alkyl iodides, alkyl fluorides or mixtures thereof.

12. The process as claimed in claim 11, wherein said alkyl halide is an alkyl iodide selected from methyl iodide, ethyl iodide or propyl iodide.

13. The process as claimed in claim 1, wherein said suitable coupling reagent is selected from I-(3-dimethylaminopropyl)-3-ethylcarbodiimide hydrochloride (EDC), dicyclohexylcarbodiimide (DCC), I-cyclohexyl-3-(2-morpholmoethyl)carbodiimide, 1,3-di-tert-butylcarbodiimide, I-(dimethylaminopropyl)-3-ethylcarbodiimide methiodide, I-tert-butyl-3-(1ùphenylmethyl)-carbodiimide, 1,3-diisopropylcarbodiimide, bis-(diphenylmethyl)-carbodiimide, I-tert-butyl-3-ethylcarbodiimide, 1-methyl-2-chloropyridinium iodide, 2-ethoxy-1-ethoxycarbonyl-I,2-dihydroquinoline (EEDQ), BOP-chloride or isobutyl chloroformate.

14. The process as claimed in claim 1, wherein $R^{3a}$ and $R^{3b}$ of said suitable amine are independently selected from hydrogen, $C_1$-$C_4$ alkyl or $C_3$-$C_6$ cycloalkyl-$C_1$-$C_4$ alkyl.

15. The process as claimed in claim 1, wherein said suitable acid is selected from hydrochloric acid, hydrobromic acid, sulfuric acid, formic acid, acetic acid, trifluoroacetic acid, propionic acid, methanesulfonic acid, benzenesulfonic acid, p-toluenesulfonic acid, an acidic ion-exchange resin or mixture thereof.

16. The process as claimed in claim 1, wherein said suitable base is selected from ammonia, alkali or alkaline earth metal hydroxide or carbonate or bicarbonate, methylamine, dimethyl amine, diethyl amine, triethylamine, diisopropylamine, diisopropyl ethyl amine, pyridine, alkylated and dialkylated pyridines, dimethylamino pyridine, piperidine or mixtures thereof.

17. The process as claimed in claim 16, wherein said alkali or alkaline earth metal is selected from lithium, sodium, potassium, rubidium, caesium, calcium, magnesium, barium or mixtures thereof.

18. The process as claimed in claim 1, where in the compound of formula (I), $R^1$ is $CH_3$, Br or Cl; $R^2$ is CN, Br or Cl; $R^{3a}$ is H; $R^{3b}$ is methyl or 1-cyclopropyl ethyl; $R^{3c}$ is H; $R^4$ is Br or

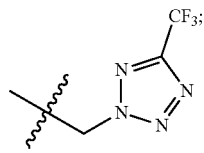 [SMILES: *Cn1nnc(C(F)(F)F)n1]

$R^5$ is Cl; $R^6$ is H or Cl; and Z is N.

19. The process as claimed in claim 1, where in the anthranilic diamide of formula (VI), $R^1$ is $CH_3$, Br or Cl; $R^2$ is CN, Br or Cl; $R^{3a}$ is H; $R^{3b}$ is methyl or 1-cyclopropyl ethyl; and $R^{3c}$ is H.

* * * * *